United States Patent
Toida

[19]

[11] Patent Number: 5,810,719
[45] Date of Patent: Sep. 22, 1998

[54] ENDOSCOPE

[75] Inventor: Masahiro Toida, Kanagawa-ken, Japan

[73] Assignee: Fuji Photo Film Co., Ltd., Kanagawa-ken, Japan

[21] Appl. No.: 665,640

[22] Filed: Jun. 18, 1996

Related U.S. Application Data

[63] Continuation of Ser. No. 111,772, Aug. 25, 1993, abandoned.

[30] Foreign Application Priority Data

| Aug. 25, 1992 | [JP] | Japan | 4-225428 |
| Aug. 25, 1992 | [JP] | Japan | 4-225429 |
| Aug. 28, 1992 | [JP] | Japan | 4-229794 |

[51] Int. Cl.$^6$ ........................................ A61B 1/04
[52] U.S. Cl. .................. 600/160; 600/477; 600/478; 356/345
[58] Field of Search ................. 600/182, 160, 600/117, 103, 477, 478; 128/665, 664; 359/1, 3, 10, 15; 348/6, 7, 40, 41; 356/4, 5, 345, 351, 352, 355, 359, 360

[56] References Cited

U.S. PATENT DOCUMENTS

| 4,479,499 | 10/1984 | Alfano | 356/341 X |
| 4,824,251 | 4/1989 | Slotwinski et al. | 356/4.5 |
| 4,928,005 | 5/1990 | Lefevre et al. | 356/345 |
| 5,170,217 | 12/1992 | Nishimoto | 356/345 |
| 5,291,267 | 3/1994 | Sorin et al. | 356/345 |
| 5,305,759 | 4/1994 | Kaneko et al. | 128/665 |
| 5,321,501 | 6/1994 | Swanson et al. | 356/345 |
| 5,349,440 | 9/1994 | DeGroot | 356/349 |
| 5,434,669 | 7/1995 | Tabata et al. | 600/160 |

FOREIGN PATENT DOCUMENTS

| 61-188513 | 8/1986 | Japan | 600/182 |

*Primary Examiner*—Gene Mancene
*Assistant Examiner*—John P. Leubecker
*Attorney, Agent, or Firm*—Sughrue, Mion, Zinn, Macpeak & Seas, PLLC

[57] ABSTRACT

A deep portion visualizing endoscope comprises a flexible fiber bundle, into which a laser beam produced by a frequency-sweep single frequency laser beam source is entered. The laser beam is irradiated from a radiating end of the fiber bundle to the region inside of a sample to be viewed, and is reflected from reflection planes of the sample. The reflected laser beam interferes with a laser beam, which has been split from the laser beam before being reflected from the reflection planes and which has traveled by a predetermined optical path length, and an image signal is thereby obtained. The image signal is composed of a plurality of difference-frequency beat signals such that the frequencies, at which the signal intensities repeatedly become high and low, may vary in accordance with the difference between depths of the reflection planes from the inner surface of the sample. A beat signal, the intensity of which repeatedly becomes high and low at a predetermined frequency, is then discriminated from the image signal. An image of a reflection plane at a specific depth is reproduced from the discriminated beat signal.

4 Claims, 14 Drawing Sheets

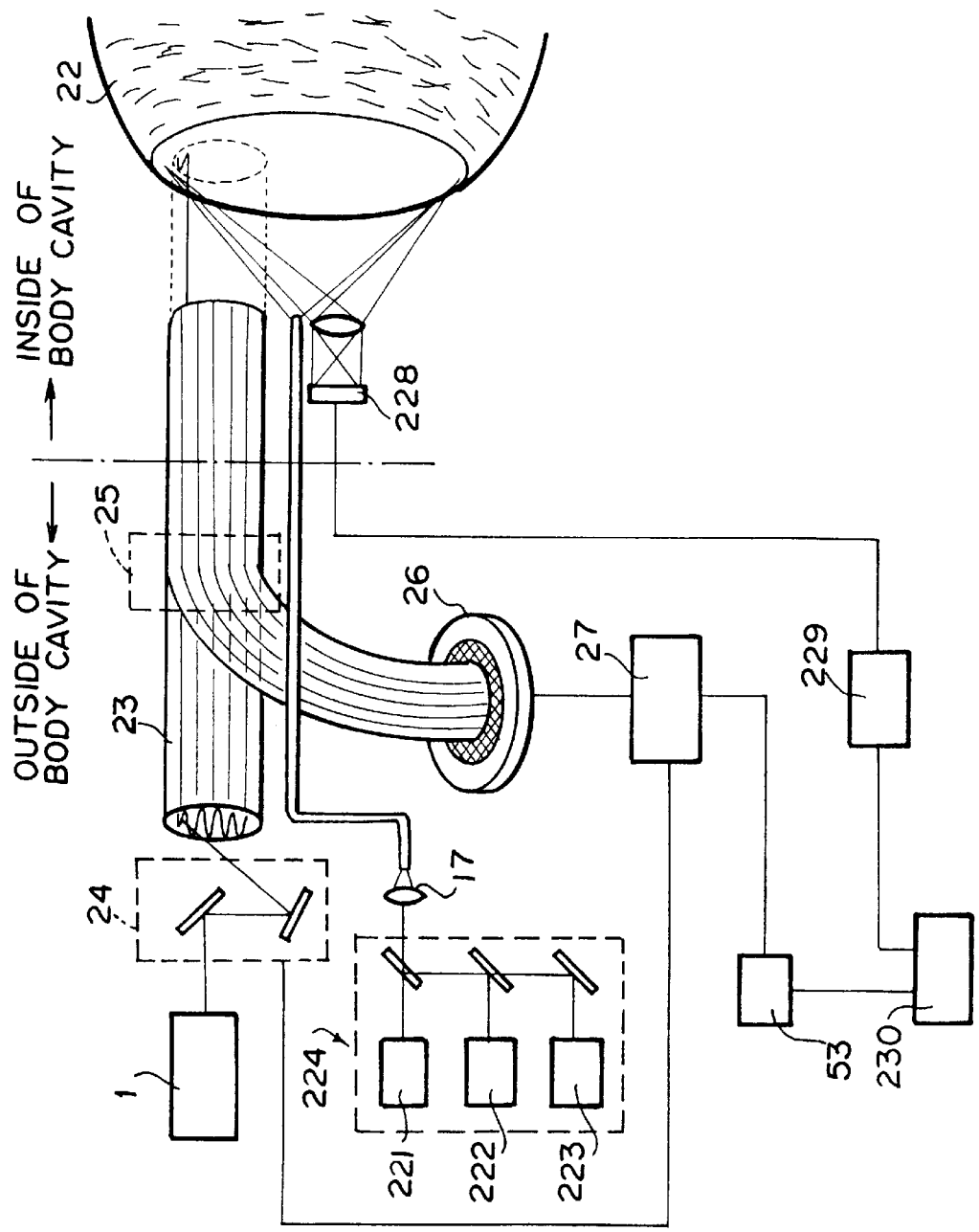

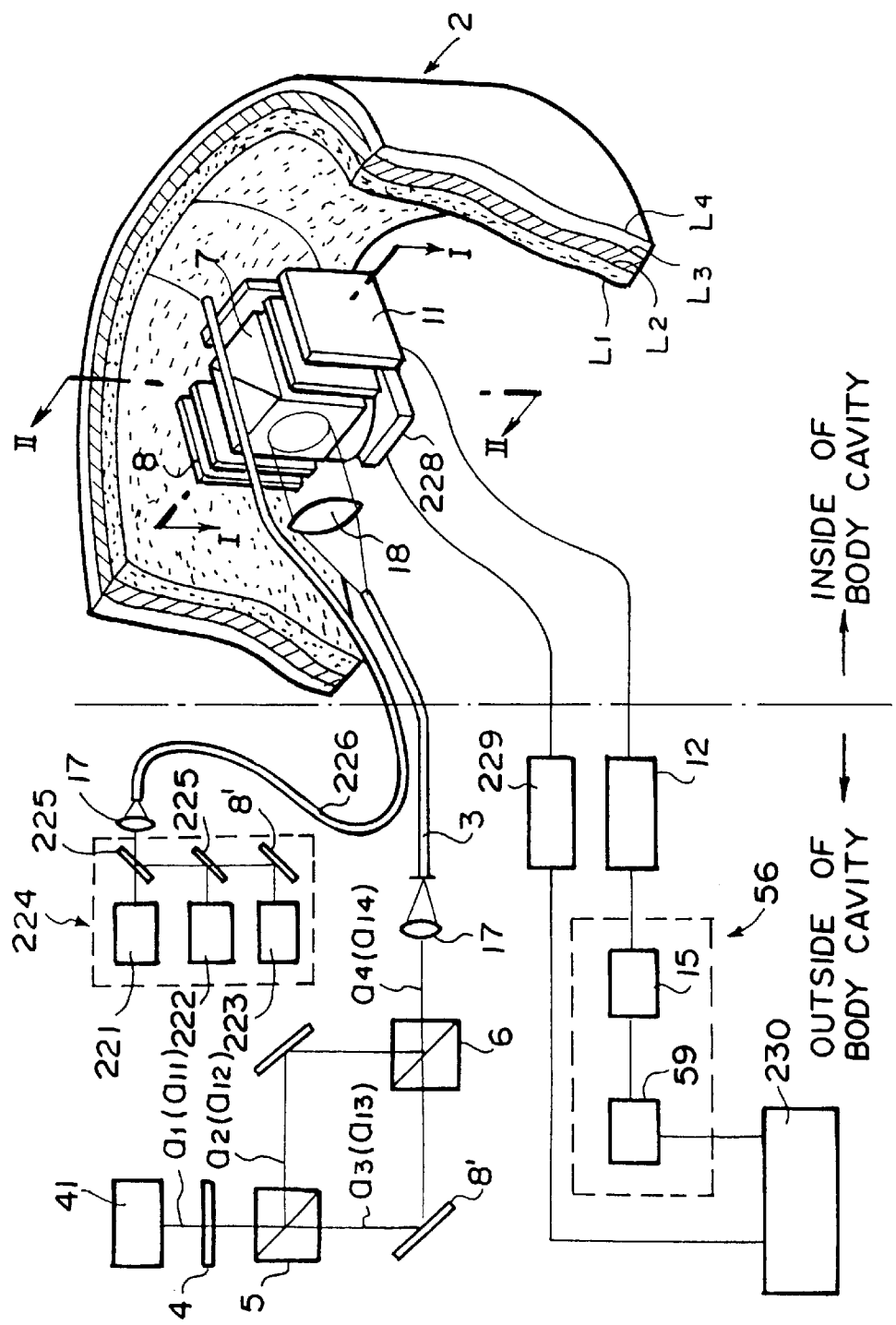

ENDOSCOPE

This is a Continuation of application Ser. No. 08/111,772 filed Aug. 25, 1993, now abandoned.

BACKGROUND OF THE INVENTION

1. Field of the Invention

This invention relates to an endoscope for primarily visualizing the inner surface of the body cavity of a living body. This invention particularly relates to an endoscope for visualizing the forms, structures, constituents and/or functions of the inner surface of the body cavity and deep portions of the body cavity, which portions are deep from the inner surface of the body cavity. This invention also relates to an endoscope for obtaining an image composed from a visible image of the inner surface of the body cavity and each of images representing the forms, structures, constituents and/or functions of the inner surface and deep portions of the body cavity.

2. Description of the Prior Art

As endoscopes for visualizing the regions inside of samples, i.e. inner surfaces of body cavities of living bodies, and the like, fiberscopes utilizing optical fibers have heretofore been used.

The fiberscope is provided with an illuminating light source and an image input means, which are located at one end of a flexible bundle of optical fibers. The fiberscope is also provided with an image output means, which is located at the other end of the optical fiber bundle. The image output means feeds out an image, which has been fed into the image input means, via the optical fibers to the exterior. The one end side of the optical fiber bundle is inserted into the body cavity, and illuminating light is produced by the illuminating light source and irradiated to the inner surface of the body cavity. An image formed by the light, which has been reflected by the inner surface of the body cavity, is fed into the image input means, transmitted through the optical fibers extending to the region outside of the body cavity, and fed out from the image output means. In this manner, the inner surface of the body cavity is viewed in a real time fashion from the region outside of the body cavity.

As described above, the fiberscope enables the real time viewing of the region inside of the body cavity. The fiberscope also enables examinations utilizing forceps channels and medical treatment utilizing electricity, microwaves, laser beams, and the like.

Electron endoscopes utilizing the recently rapidly advanced electronic technology and image processing technology have also heretofore been used.

The electron endoscope is provided with a charge coupled device (CCD) in lieu of the image input means of the fiberscope. An image taken up by the endoscope is converted into an electric signal. The electric signal is transmitted through a transmission medium and is fed out from an image output means. The image is then reconstructed by a video processor.

As described above, with the electron endoscope, an image taken up by the endoscope can be obtained as an electric signal. Therefore, the electron endoscope is advantageous for communication characteristics, such as image filing and transmission characteristics, and image processing characteristics.

With the rapid advances made in medical treatment and diagnostic techniques utilizing endoscopes in recent years, there has arisen a strong demand for endoscopes capable of providing a wide variety of information.

For example, if information representing the form, the structure, constituents and/or functions of a portion under a mucous membrane at the surface of a digestive organ is obtained, a diseased part, which cannot be viewed from the surface of the digestive organ, can be detected. Therefore, it becomes possible to detect and treat the disease in its early stages.

Also, investigating the relationship between the information, which represents constituents and/or functions, and the diseased part is very useful in clarifying the mechanisms of occurrence and progress of various diseases.

However, with the conventional endoscopes described above, only the visible surface image of the region inside of the body cavity, which image is formed with light reflected from the inner surface of the body cavity, can be viewed. With the conventional endoscopes described above, information representing the forms, structures, constituents and/or functions of portions deep from the inner surface of the body cavity cannot be obtained.

SUMMARY OF THE INVENTION

The primary object of the present invention is to provide a deep portion visualizing endoscope, which is capable of visualizing the forms and/or structures of the inner surface of the body cavity and deep portions of the body cavity, which portions are deep from the inner surface of the body cavity.

Another object of the present invention is to provide a function diagnosing endoscope, which is capable of visualizing constituents and/or functions of the inner surface of the body cavity and deep portions of the body cavity, which portions are deep from the inner surface of the body cavity.

The specific object of the present invention is to provide an image composing endoscope, which obtains and displays an image composed from a surface image representing the shape of the inner surface of the body cavity and each of deep portion images representing the forms, structures, constituents and/or functions of not only the inner surface but also deep portions of the body cavity.

The present invention provides a first deep portion visualizing endoscope. Specifically, the present invention provides, in an endoscope comprising:

i) a flexible fiber bundle having an entry end, from which light is entered into the fiber bundle, and a radiating end, from which the light having been entered into the fiber bundle is radiated out and which is inserted into the region inside of a sample to be viewed, ii) a light source for producing the light, which is to be entered into the fiber bundle from the entry end, and iii) an image forming means for irradiating the light, which has been radiated out of the radiating end of the fiber bundle, to the region inside of the sample, and thereby obtaining a two-dimensional image of the region inside of the sample, a deep portion visualizing endoscope, wherein the light source is a frequency-sweep single frequency laser beam source, which produces a laser beam to be entered into the fiber bundle from the entry end, and the image forming means comprises:

a) an image signal forming means for causing the laser beam, which has been irradiated to the region inside of the sample and which has then been reflected from reflection planes of the sample, and the laser beam, which has been split from the laser beam before being reflected from the reflection planes of the sample and which has traveled by a predetermined optical path length, to interfere with each other, and thereby obtaining an image signal composed of a plurality of kinds of difference-frequency beat signals such that the frequencies, at which the intensities of the difference-frequency beat signals repeatedly become high and low, may vary in accordance with the difference between depths of the reflection planes from the inner surface of the sample, and b) an image reproducing means for discriminating a difference-frequency beat signal, the intensity of which repeatedly becomes high and low at a predetermined frequency, from the image signal, and reproducing an image of a reflection plane, which is located at a predetermined depth from the inner surface of the sample, from the discriminated difference-frequency beat signal.

The present invention also provides a second deep portion visualizing endoscope, wherein the first deep portion visualizing endoscope in accordance with the present invention is modified such that the image signal forming means comprises:

1) an optical path splitting means for splitting the laser beam before being entered into the fiber bundle from the entry end into two laser beams having planes of polarization, which planes of polarization are approximately normal to each other, 2) a first wavefront matching means for matching the wave fronts of the two laser beams, which have been split by the optical path splitting means, with each other before the two split laser beams are entered into the fiber bundle from the entry end, a wavefront-matched laser beam being thereby obtained, 3) a second wavefront matching means for splitting the wavefront-matched laser beam, which has been radiated out of the radiating end of the fiber bundle, into two laser beams having planes of polarization, which planes of polarization are approximately normal to each other, such that one of the two split laser beams may travel by the predetermined optical path length, and such that the other laser beam may be irradiated to and reflected by the sample, the second wavefront matching means thereafter matching the wave front of the laser beam, which has traveled by the predetermined optical path length, with the wave front of the laser beam, which has been irradiated to and reflected by the sample, 4) a polarization means for causing the components of the two laser beams subjected to the wavefront matching by the second wavefront matching means, which components have an identical direction of polarization, to interfere with each other, and 5) a two-dimensional optical intensity detecting means for detecting a plurality of kinds of difference-frequency beat signals obtained from the interference such that the frequencies, at which the intensities of the difference-frequency beat signals repeatedly become high and low, may vary, and the image reproducing means comprises:

1) a frequency analyzing means for discriminating a difference-frequency beat signal, the intensity of which repeatedly becomes high and low at a predetermined frequency, from the plurality of kinds of the difference-frequency beat signals, 2) a reconstruction means for reconstructing an image of a portion, which is located at a specific depth from the inner surface of the sample, from the discriminated difference-frequency beat signal, the intensity of which repeatedly becomes high and low at the predetermined frequency, and 3) an image output means, which outputs the image having been reconstructed by the reconstruction means.

The present invention further provides a third deep portion visualizing endoscope, wherein the second deep portion visualizing endoscope in accordance with the present invention is modified such that a rotation means is provided which rotates the second wavefront matching means, the polarization means, and the two-dimensional optical intensity detecting means together around an axis, which is approximately parallel to the optical path of the laser beam having been radiated out of the radiating end of the fiber bundle.

The present invention still further provides a fourth deep portion visualizing endoscope, wherein the first deep portion visualizing endoscope in accordance with the present invention is modified such that the fiber bundle is a single mode image fiber bundle, the image signal forming means comprises:

1) a scanning means for causing the laser beam, which has been produced by the frequency-sweep single frequency laser beam source, to impinge sequentially upon entry ends of a plurality of image fibers constituting the image fiber bundle, 2) a fiber interference system located in an optical path of each image fiber in order to split the laser beam having been entered into the image fiber from its entry end into a laser beam, which travels by the predetermined optical path length, and a laser beam, which is radiated out of a radiating end of the image fiber, the fiber interference system thereafter causing the laser beam, which has traveled by the predetermined optical path length, and the laser beam, which has been reflected by the sample after being radiated out of the image fiber and which has then entered into the image fiber from the radiating end, to interfere with each other, and 3) a two-dimensional optical intensity detecting means for detecting a plurality of kinds of difference-frequency beat signals obtained from the interference such that the frequencies, at which the intensities of the difference-frequency beat signals repeatedly become high and low, may vary, and the image reproducing means comprises:

1) a frequency analyzing means for discriminating a difference-frequency beat signal, the intensity of which repeatedly becomes high and low at a predetermined frequency, from the plurality of kinds of the difference-frequency beat signals, 2) a reconstruction means for reconstructing an image of a portion, which is located at a specific depth from the inner surface of the sample, from the discriminated difference-frequency beat signal, the intensity of which repeatedly becomes high and low at the predetermined frequency, and 3) an image output means, which outputs the image having been reconstructed by the reconstruction means.

With the deep portion visualizing endoscopes in accordance with the present invention, the laser beam, the frequency of which is swept with the passage of time, is produced by the frequency-sweep single frequency laser beam source. The laser beam is entered into the fiber bundle from its entry end and transmitted to its radiating end, which is inserted into the region inside of the sample. The laser beam is then radiated out of the radiating end of the fiber bundle and irradiated to the region inside of the sample.

The laser beam, which has been produced by the laser beam source, is split into two laser beams before the laser beam is irradiated to the region inside of the sample, i.e. immediately after it has been produced by the laser beam source, during its travel inside of the fiber bundle, or immediately after it has been radiated out of the fiber bundle. One of the two split laser beams is not irradiated to the region inside of the sample and is caused to travel by the predetermined optical path length.

The laser beam, which has been radiated out of the radiating end of the fiber bundle and has been irradiated to the region inside of the sample, is reflected from a plurality of reflection planes, which are located at the inner surface of the sample and at portions deep from the inner surface. A plurality of laser beams having been reflected from the plurality of the reflection planes, which are located at the inner surface of the sample and at portions deep from the inner surface, and the laser beam, which has traveled by the predetermined optical path length, are caused to interfere with each other by the image forming means.

The optical path lengths, by which the laser beams having been reflected from the reflection planes located at the inner surface of the sample and at portions deep from the inner surface of the sample have traveled, vary in accordance with the difference between the depths of the reflection planes from the inner surface of the sample. Specifically, the time required to reach the image forming means varies for different laser beams reflected from different depths with respect to the inner surface of the sample.

In such cases, the frequency of the laser beam having been produced by the laser beam source is swept with the passage of time. Therefore, at the time at which one of the laser beams having been reflected from different reflection planes of the sample arrives at the image forming means, the frequency of the laser beam having traveled by the predetermined optical path length is determined by the difference between the optical path lengths of the two laser beams and a function of the frequency with respect to the frequency sweep time which has occurred.

As described above, the laser beam, which has arrived at the image forming means after traveling by the predetermined optical path length, and the laser beam, which has arrived at the image forming means after being reflected by one of different reflection planes of the sample, vary in the frequency. Therefore, when these two laser beams are caused to interfere with each other by the image forming means, a difference-frequency beat signal occurs. The intensity of the difference-frequency beat signal repeatedly becomes high and low at a frequency equal to the difference between the frequencies of the two laser beams.

In the manner described above, a plurality of kinds of difference-frequency beat signals occur such that the frequencies, at which the intensities of the difference-frequency beat signals repeatedly become high and low, may vary in accordance with the difference between the depths of the reflection planes from the inner surface of the sample. The image reproducing means discriminates a difference-frequency beat signal, the intensity of which repeatedly becomes high and low at a predetermined frequency, from the plurality of kinds of the difference-frequency beat signals occurring such that the frequencies, at which the intensities of the difference-frequency beat signals repeatedly become high and low, may vary. In this manner, a laser beam, which has been reflected from a reflection plane located at a predetermined depth in the sample, can be sorted out. Also, from the intensity of the laser beam, which has been reflected from the reflection plane located at the predetermined depth in the sample, information representing the light absorption at the reflection plane can be obtained. Therefore, with the image reproducing means, a two-dimensional plane image representing the information at the predetermined depth in the sample can be obtained from the reflected laser beam.

As described above, with the deep portion visualizing endoscopes in accordance with the present invention, portions deep from the inner surface of the body cavity, which could not be viewed with the conventional endoscopes, can be visualized as plane images or tomographic images representing information at specific depths. Therefore, the deep portion visualizing endoscopes in accordance with the present invention are advantageous in that, for example, diseased parts occurring at positions deep from the inner surface of the body cavity can be detected in their early stages.

The present invention also provides a first function diagnosing endoscope. Specifically, the present invention also provides, in an endoscope comprising:

i) a flexible fiber bundle having an entry end, from which light is entered into the fiber bundle, and a radiating end, from which the light having been entered into the fiber bundle is radiated out and which is inserted into the region inside of a sample to be viewed, ii) a light source for producing the light, which is to be entered into the fiber bundle from the entry end, and iii) an image forming means for irradiating the light, which has been radiated out of the radiating end of the fiber bundle, to the region inside of the sample, and thereby obtaining a two-dimensional image of the region inside of the sample, a function diagnosing endoscope, wherein the light source is a frequency-sweep laser beam source capable of producing at least two laser beams having different frequencies, which laser beams are to be sequentially entered into the fiber bundle from the entry end, the frequencies of the laser beams being swept with the passage of time, and the image forming means comprises:

a) an image signal forming means for causing a laser beam, which has been irradiated to the region inside of the sample and which has then been reflected from reflection planes of the sample, and the laser beam, which has been split from the laser beam before being reflected from the reflection planes of the sample and which has traveled by a predetermined optical path length, to interfere with each other, and thereby obtaining an image signal composed of a plurality of kinds of difference-frequency beat signals such that the frequencies, at which the intensities of the difference-frequency beat signals repeatedly become high and low, may vary in accordance with the difference between depths of the reflection planes from the inner surface of the sample, and b) an image reproducing means for discriminating a difference-frequency beat signal, the intensity of which repeatedly becomes high and low at a predetermined frequency, from the image signal, and calculating values concerning constituents and/or functions of a reflection plane, which is located at a predetermined depth from the inner surface of the sample, from at least two discriminated difference-frequency beat signals, the intensities of which repeatedly become high and low at predetermined frequencies and which are obtained when at least two laser beams having different frequencies are respectively irradiated to the sample, the image reproducing means thereafter reproducing an image, which represents constituents and/or functions of the sample, from the calculated values.

The present invention further provides a second function diagnosing endoscope, wherein the first function diagnosing endoscope in accordance with the present invention is modified such that the image signal forming means comprises:

1) an optical path splitting means for splitting the laser beam before being entered into the fiber bundle from the entry end into two laser beams having planes of polarization, which planes of polarization are approximately normal to each other, 2) a first wavefront matching means for matching the wave fronts of the two laser beams, which have been split by the optical path splitting means, with each other before the two split laser beams are entered into the fiber bundle from the entry end, a wavefront-matched laser beam being thereby obtained, 3) a second wavefront matching means for splitting the wavefront-matched laser beam, which has been radiated out of the radiating end of the fiber bundle, into two laser beams having planes of polarization, which planes of polarization are approximately normal to each other, such that one of the two split laser beams may travel by the predetermined optical path length, and such that the other laser beam may be irradiated to and reflected by the sample, the second wavefront matching means thereafter matching the wave front of the laser beam, which has traveled by the predetermined optical path length, with the wave front of the laser beam, which has been irradiated to and reflected by the sample, 4) a polarization means for causing the components of the two laser beams subjected to the wavefront matching by the second wavefront matching means, which components have an identical direction of polarization, to interfere with each other, and 5) a two-dimensional optical intensity detecting means for detecting a plurality of kinds of difference-frequency beat signals obtained from the interference such that the frequencies, at which the intensities of the difference-frequency beat signals repeatedly become high and low, may vary, and the image reproducing means comprises:

1) a frequency analyzing means for discriminating a difference-frequency beat signal, the intensity of which repeatedly becomes high and low at a predetermined frequency, from the plurality of kinds of the difference-frequency beat signals, 2) a reconstruction means for calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when at least two laser beams having different frequencies are respectively irradiated to the sample, the reconstruction means thereafter reconstructing an image, which represents constituents and/or functions of the portion located at the specific depth from the inner surface of the sample, from the calculated values, and 3) an image output means, which outputs the image having been reconstructed by the reconstruction means.

The present invention still further provides a third function diagnosing endoscope, wherein the second function diagnosing endoscope in accordance with the present invention is modified such that a rotation means is provided which rotates the second wavefront matching means, the polarization means, and the two-dimensional optical intensity detecting means together around an axis, which is approximately parallel to the optical path of the laser beam having been radiated out of the radiating end of the fiber bundle.

The present invention also provides a fourth function diagnosing endoscope, wherein the first function diagnosing endoscope in accordance with the present invention is modified such that the fiber bundle is a single mode image fiber bundle, the image signal forming means comprises:

1) a scanning means for causing the laser beam, which has been produced by the frequency-sweep laser beam source, to impinge sequentially upon entry ends of a plurality of image fibers constituting the image fiber bundle, 2) a fiber interference system located in an optical path of each image fiber in order to split the laser beam having been entered into the image fiber from its entry end into a laser beam, which travels by the predetermined optical path length, and a laser beam, which is radiated out of a radiating end of the image fiber, the fiber interference system thereafter causing the laser beam, which has traveled by the predetermined optical path length, and the laser beam, which has been reflected by the sample after being radiated out of the image fiber and which has then entered into the image fiber from the radiating end, to interfere with each other, and 3) a two-dimensional optical intensity detecting means for detecting a plurality of kinds of difference-frequency beat signals obtained from the interference such that the frequencies, at which the intensities of the difference-frequency beat signals repeatedly become high and low, may vary, and the image reproducing means comprises:

1) a frequency analyzing means for discriminating a difference-frequency beat signal, the intensity of which repeatedly becomes high and low at a predetermined frequency, from the plurality of kinds of the difference-frequency beat signals, 2) a reconstruction means for calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when at least two laser beams having different frequencies are respectively irradiated to the sample, the reconstruction means thereafter reconstructing an image, which represents constituents and/or functions of the portion located at the specific depth from the inner surface of the sample, from the calculated values, and 3) an image output means, which outputs the image having been reconstructed by the reconstruction means.

The function diagnosing endoscopes in accordance with the present invention are provided with the frequency-sweep laser beam source capable of producing at least two laser beams having different frequencies such that the frequencies of the laser beams may be swept with the passage of time. Specifically, the frequency-sweep laser beam source has at least two frequency bands, in which the frequency is swept.

With the function diagnosing endoscopes in accordance with the present invention, the laser beam, the frequency of which is swept with the passage of time, is produced by the frequency-sweep laser beam source. The laser beam is entered into the fiber bundle from its entry end and transmitted to its radiating end, which is inserted into the region inside of the sample. The laser beam is then radiated out of the radiating end of the fiber bundle and irradiated to the region inside of the sample.

In the same manner as that for the aforesaid deep portion visualizing endoscopes in accordance with the present invention, the laser beam, which has arrived at the image forming means after traveling by the predetermined optical path length, and the laser beam, which has arrived at the image forming means after being reflected by one of different reflection planes of the sample, are caused to interfere with each other by the image forming means. As a result of the interference, a difference-frequency beat signal is obtained. The intensity of the difference-frequency beat signal repeatedly becomes high and low at a frequency, which is equal to the difference between the frequencies of the two laser beams.

In the manner described above, a plurality of kinds of difference-frequency beat signals occur such that the frequencies, at which the intensities of the difference-frequency beat signals repeatedly become high and low, may vary in accordance with the difference between the depths of the reflection planes from the inner surface of the sample.

The image reproducing means discriminates a difference-frequency beat signal, the intensity of which repeatedly becomes high and low at a predetermined frequency, from the plurality of kinds of the difference-frequency beat signals occurring such that the frequencies, at which the intensities of the difference-frequency beat signals repeatedly become high and low, may vary. In this manner, a laser beam, which has been reflected from a reflection plane located at a specific depth in the sample, can be sorted out.

Also, the intensity of the laser beam, which has been reflected from the reflection plane located at the specific depth in the sample, represents the information concerning the light reflection or light absorption at the deep portion of the sample, from which the laser beam has been reflected.

The operations described above are repeated by using at least two laser beams having different frequencies, and at least two discriminated difference-frequency beat signals are thereby obtained. With the image reproducing means, the values concerning constituents and/or functions of the reflection plane, which is located at the predetermined depth from the inner surface of the sample, are calculated from at least two discriminated difference-frequency beat signals. A two-dimensional plane image representing the constituents and/or functions of the reflection plane at the predetermined depth in the sample can then be obtained from the calculated values.

The discrimination of the difference-frequency beat signal, the intensity of which repeatedly becomes high and low at a predetermined frequency, from the plurality of kinds of the difference-frequency beat signals may be carried out for all of the plural kinds of frequencies. In this manner, a tomographic image of the sample can be obtained.

As described above, with the function diagnosing endoscopes in accordance with the present invention, the constituents and/or functions at the inner surface and portions deep from the inner surface of the body cavity, which could not be visualized with the conventional endoscopes, can be visualized as plane images or tomographic images representing information at specific depths. Therefore, the function diagnosing endoscopes in accordance with the present invention are advantageous in that, for example, diseased parts occurring at positions deep from the inner surface of the body cavity can be detected in their early stages.

The present invention further provides a first image composing endoscope comprising:

i) a deep portion image output system comprising:
   a) a first flexible fiber bundle having an entry end, from which light is entered into the fiber bundle, and a radiating end, from which the light having been entered into the fiber bundle is radiated out and which is inserted into the region inside of a sample to be viewed,
   b) a first light source for producing the light, which is to be entered into the first fiber bundle from the entry end, and
   c) a deep portion image output means for irradiating the light, which has been radiated out of the radiating end of the first fiber bundle, to the region inside of the sample such that the light may reach portions deep from the inner surface of the sample in the region inside of the sample, and thereby generating a deep portion image signal representing a deep portion image of the region inside of the sample, ii) a surface image output system comprising:
   a) a second flexible fiber bundle having an entry end, from which light is entered into the fiber bundle, and a radiating end, from which the light having been entered into the fiber bundle is radiated out and which is inserted into the region inside of a sample to be viewed,
   b) a second light source for producing the light, which is to be entered into the second fiber bundle from the entry end, and
   c) a surface image output means for irradiating the light, which has been radiated out of the radiating end of the second fiber bundle, to the region inside of the sample, and thereby generating a surface image signal representing a surface image of the region inside of the sample, and
   iii) an image composing and displaying means for composing an image from the deep portion image, which is represented by the deep portion image signal obtained from the deep portion image output system, and the surface image, which is represented by the surface image signal obtained from the surface image output system, and displaying the composed image.

The present invention still further provides a second image composing endoscope, wherein the first image composing endoscope in accordance with the present invention is modified such that the first light source of the deep portion image output system is a frequency-sweep single frequency laser beam source capable of producing a laser beam to be entered into the first fiber bundle from the entry end, the frequency of the laser beam being swept with the passage of time, and the deep portion image output means of the deep portion image output system comprises:
   1) a deep portion image signal forming means for causing the laser beam, which has been irradiated to the region inside of the sample and which has then been reflected from reflection planes of the sample, and the laser beam, which has been split from the laser beam before being reflected from the reflection planes of the sample and which has traveled by a predetermined optical path length, to interfere with each other, and thereby obtaining a plurality of kinds of difference-frequency beat signals such that the frequencies, at which the intensities of the difference-frequency beat signals repeatedly become high and low, may vary in accordance with the difference between depths of the reflection planes from the inner surface of the sample, and 2) a deep portion image signal output means for discriminating a difference-frequency beat signal, the intensity of which repeatedly becomes high and low at a predetermined frequency, from the plurality of kinds of the difference-frequency beat signals, and generating a deep portion image signal, which represents the form and/or structure of a portion located at a specific depth from the inner surface of the sample, from the optical intensity of the discriminated difference-frequency beat signal, the intensity of which repeatedly becomes high and low at the predetermined frequency.

The present invention also provides a third image composing endoscope, wherein the second image composing endoscope in accordance with the present invention is modified such that the first fiber bundle is constituted of single mode fibers, the deep portion image signal forming means comprises:
(1) an optical path splitting means for splitting the laser beam before being entered into the first fiber bundle from the entry end into two laser beams having planes of polarization, which planes of polarization are approximately normal to each other,
(2) a first wavefront matching means for matching the wave fronts of the two laser beams, which have been split by the optical path splitting means, with each other before the two split laser beams are entered into the first fiber bundle from the entry end, a wavefront-matched laser beam being thereby obtained,
(3) a second wavefront matching means for splitting the wavefront-matched laser beam, which has been radiated out of the radiating end of the first fiber bundle, into two laser beams having planes of polarization, which planes of polarization are approximately normal to each other, such that one of the two split laser beams may travel by the predetermined optical path length, and such that the other laser beam may be irradiated to and reflected by the sample, the second wavefront matching means thereafter matching the wave front of the laser beam, which has traveled by the predetermined optical path length, with the wave front of the laser beam, which has been irradiated to and reflected by the sample,
(4) a polarization means for causing the components of the two laser beams subjected to the wavefront matching by the second wavefront matching means, which components have an identical direction of polarization, to interfere with each other, and
(5) a two-dimensional optical intensity detecting means for detecting a plurality of kinds of difference-frequency beat signals obtained from the interference such that the frequencies, at which the intensities of the difference-frequency beat signals repeatedly become high and low, may vary, and the deep portion image signal output means comprises:
(1) a frequency analyzing means for discriminating a difference-frequency beat signal, the intensity of which repeatedly becomes high and low at a predetermined frequency, from the plurality of kinds of the difference-frequency beat signals, and
(2) a reconstruction means for generating an image signal, which represents the form and/or structure of a portion located at a specific depth from the inner surface of the sample, from the discriminated difference-frequency beat signal, the intensity of which repeatedly becomes high and low at the predetermined frequency.

The present invention further provides a fourth image composing endoscope, wherein the second image composing endoscope in accordance with the present invention is modified such that the first fiber bundle is a single mode image fiber bundle, the deep portion image signal forming means comprises:
(1) a scanning means for causing the laser beam, which has been produced by the frequency-sweep single frequency laser beam source, to impinge sequentially upon entry ends of a plurality of image fibers constituting the image fiber bundle,
(2) a fiber interference system located in an optical path of each image fiber in order to split the laser beam having been entered into the image fiber from its entry end into a laser beam, which travels by the predetermined optical path length, and a laser beam, which is radiated out of a radiating end of the image fiber, the fiber interference system thereafter causing the laser beam, which has traveled by the predetermined optical path length, and the laser beam, which has been reflected by the sample after being radiated out of the image fiber and which has then entered into the image fiber from the radiating end, to interfere with each other, and
(3) a two-dimensional optical intensity detecting means for detecting a plurality of kinds of difference-frequency beat signals obtained from the interference such that the frequencies, at which the intensities of the difference-frequency beat signals repeatedly become high and low, may vary, and the deep portion image signal output means comprises:
(1) a frequency analyzing means for discriminating a difference-frequency beat signal, the intensity of which repeatedly becomes high and low at a predetermined frequency, from the plurality of kinds of the difference-frequency beat signals, and
(2) a reconstruction means for generating an image signal, which represents the form and/or structure of a portion located at a specific depth from the inner surface of the sample, from the discriminated difference-frequency beat signal, the intensity of which repeatedly becomes high and low at the predetermined frequency.

The present invention still further provides a fifth image composing endoscope, wherein the first image composing endoscope in accordance with the present invention is modified such that the first light source of the deep portion image output system is a frequency-sweep laser beam source capable of producing at least two laser beams having different frequencies, which laser beams are to be sequentially entered into the first fiber bundle from the entry end, the frequencies of the laser beams being swept with the passage of time, and the deep portion image output means of the deep portion image output system comprises:

1) a deep portion image signal forming means for causing a laser beam, which has been irradiated to the region inside of the sample and which has then been reflected from reflection planes of the sample, and the laser beam, which has been split from the laser beam before being reflected from the reflection planes of the sample and which has traveled by a predetermined optical path length, to interfere with each other, and thereby obtaining a plurality of kinds of difference-frequency beat signals such that the frequencies, at which the intensities of the difference-frequency beat signals repeatedly become high and low, may vary in accordance with the difference between depths of the reflection planes from the inner surface of the sample, and 2) a deep portion image signal output means for discriminating a difference-frequency beat signal, the intensity of which repeatedly becomes high and low at a predetermined frequency, from the plurality of kinds of the difference-frequency beat signals, and calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when at least two laser beams having different frequencies and having been produced by the frequency-sweep laser beam source are respectively irradiated to the sample, the deep portion image signal output means thereafter generating a deep portion image signal, which represents constituents and/or functions of the portion located at the specific depth from the inner surface of the sample, from the calculated values.

The present invention also provides a sixth image composing endoscope, wherein the fifth image composing endoscope in accordance with the present invention is modified such that the first fiber bundle is constituted of single mode fibers, the deep portion image signal forming means comprises:
(1) an optical path splitting means for splitting the laser beam before being entered into the first fiber bundle from the entry end into two laser beams having planes of polarization, which planes of polarization are approximately normal to each other,
(2) a first wavefront matching means for matching the wave fronts of the two laser beams, which have been split by the optical path splitting means, with each other before the two split laser beams are entered into the first fiber bundle from the entry end, a wavefront-matched laser beam being thereby obtained,
(3) a second wavefront matching means for splitting the wavefront-matched laser beam, which has been radiated out of the radiating end of the first fiber bundle, into two laser beams having planes of polarization, which planes of polarization are approximately normal to each other, such that one of the two split laser beams may travel by the predetermined optical path length, and such that the other laser beam may be irradiated to and reflected by the sample, the second wavefront matching means thereafter matching the wave front of the laser beam, which has traveled by the predetermined optical path length, with the wave front of the laser beam, which has been irradiated to and reflected by the sample, (4) a polarization means for causing the components of the two laser beams subjected to the wavefront matching by the second wavefront matching means, which components have an identical direction of polarization, to interfere with each other, and
(5) a two-dimensional optical intensity detecting means for detecting a plurality of kinds of difference-frequency beat signals obtained from the interference such that the frequencies, at which the intensities of the difference-frequency beat signals repeatedly become high and low, may vary, and the deep portion image signal output means comprises:
(1) a frequency analyzing means for discriminating a difference-frequency beat signal, the intensity of which repeatedly becomes high and low at a predetermined frequency, from the plurality of kinds of the difference-frequency beat signals, and
(2) a reconstruction means for calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when at least two laser beams having different frequencies and having been produced by the frequency-sweep laser beam source are respectively irradiated to the sample, the reconstruction means thereafter generating a deep portion image signal, which represents constituents and/or functions of the portion located at the specific depth from the inner surface of the sample, from the calculated values.

The present invention further provides a seventh image composing endoscope, wherein the fifth image composing endoscope in accordance with the present invention is modified such that the first fiber bundle is a single mode image fiber bundle, the deep portion image signal forming means comprises:
(1) a scanning means for causing the laser beam, which has been produced by the frequency-sweep laser beam source, to impinge sequentially upon entry ends of a plurality of image fibers constituting the image fiber bundle,
(2) a fiber interference system located in an optical path of each image fiber in order to split the laser beam having been entered into the image fiber from its entry end into a laser beam, which travels by the predetermined optical path length, and a laser beam, which is radiated out of a radiating end of the image fiber, the fiber interference system thereafter causing the laser beam, which has traveled by the predetermined optical path length, and the laser beam, which has been reflected by the sample after being radiated out of the image fiber and which has then entered into the image fiber from the radiating end, to interfere with each other, and
(3) a two-dimensional optical intensity detecting means for detecting a plurality of kinds of difference-frequency beat signals obtained from the interference such that the frequencies, at which the intensities of the difference-frequency beat signals repeatedly become high and low, may vary, and the deep portion image signal output means comprises:
(1) a frequency analyzing means for discriminating a difference-frequency beat signal, the intensity of which repeatedly becomes high and low at a predetermined frequency, from the plurality of kinds of the difference-frequency beat signals, and (2) a reconstruction means for calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when at least two laser beams having different frequencies and having been produced by the frequency-sweep laser beam source are respectively irradiated to the sample, the reconstruction means thereafter generating a deep portion image signal, which represents constituents and/or functions of the portion located at the specific depth from the inner surface of the sample, from the calculated values.

The present invention still further provides an eighth image composing endoscope, wherein one of the first to seventh image composing endoscopes in accordance with the present invention is modified such that the second light source of the surface image output system is an RGB laser beam source, the second fiber bundle of the surface image output system is constituted of single mode fibers, and the surface image output means of the surface image output system comprises:

(1) a surface image detecting means for detecting an RGB laser beam, which has been radiated out of the radiating ends of the single mode fibers and which has then been reflected by the inner surface of the sample in the region inside of the sample, and (2) a surface image signal output means for generating a surface image signal representing a surface image of the region inside of the sample from the reflected laser beam, which has been detected by the surface image detecting means.

With the image composing endoscopes in accordance with the present invention, first light is produced by the first light source and entered into the first fiber bundle from its entry end. The light is then radiated out of the radiating end, which is inserted into the region inside of the sample.

The light, which has been radiated out of the first fiber bundle, is irradiated to the region inside of the sample such that it may reach portions deep from the inner surface of the sample. The light, which has been reflected from a plurality of reflection planes located at the deep portions, is detected by the deep portion image output means, and the deep portion image signal is thereby obtained.

Also, second light is produced by the second light source and entered into the second fiber bundle from its entry end. The light is then radiated out of the radiating end, which is inserted into the region inside of the sample.

The light, which has been radiated out of the second fiber bundle, is irradiated to the inner surface in the region inside of the sample. The light, which has been reflected from the inner surface of the sample, is detected by the surface image output means, and the surface image signal is thereby obtained.

The image composing and displaying means composes an image from the deep portion image signal and the surface image signal, which have been obtained in the manner described above. The composed image is displayed by the image composing and displaying means.

The formation of the deep portion image signal should preferably be carried out with a frequency-sweep optical heterodyne technique.

In cases where the frequency-sweep optical heterodyne technique is utilized in the deep portion image output system, the laser beam, the frequency of which is swept with the passage of time, is produced by the frequency-sweep laser beam source. The laser beam is entered into the first fiber bundle from its entry end and transmitted to its radiating end, which is inserted into the region inside of the sample. The laser beam is then radiated out of the radiating end of the first fiber bundle and irradiated to the region inside of the sample.

The laser beam, which has been produced by the laser beam source, is split into two laser beams before the laser beam is irradiated to the region inside of the sample, i.e. immediately after it has been produced by the laser beam source, during its travel inside of the first fiber bundle, or immediately after it has been radiated out of the first fiber bundle. One of the two split laser beams is not irradiated to the region inside of the sample and is caused to travel by the predetermined optical path length.

The laser beam, which has been radiated out of the radiating end of the first fiber bundle and has been irradiated to the region inside of the sample, is reflected from a plurality of reflection planes, which are located at the inner surface of the sample and at portions deep from the inner surface. A plurality of laser beams having been reflected from the plurality of the reflection planes, which are located at the inner surface of the sample and at portions deep from the inner surface, and the laser beam, which has traveled by the predetermined optical path length, are caused to interfere with each other by the deep portion image signal forming means.

The optical path lengths, by which the laser beams having been reflected from the reflection planes located at the inner surface of the sample and at portions deep from the inner surface of the sample have traveled, vary in accordance with the difference between the depths of the reflection planes from the inner surface of the sample. Specifically, the time required to reach the deep portion image signal forming means varies for different laser beams reflected from different depths with respect to the inner surface of the sample.

In such cases, the frequency of the laser beam having been produced by the laser beam source is swept with the passage of time. Therefore, at the time at which one of the laser beams having been reflected from different reflection planes of the sample arrives at the deep portion image signal forming means, the frequency of the laser beam having traveled by the predetermined optical path length is determined by the difference between the optical path lengths of the two laser beams and a function of the frequency with respect to the frequency sweep time which has occurred.

As described above, the laser beam, which has arrived at the deep portion image signal forming means after traveling by the predetermined optical path length, and the laser beam, which has arrived at the deep portion image signal forming means after being reflected by one of different reflection planes of the sample, vary in the frequency. Therefore, when these two laser beams are caused to interfere with each other by the deep portion image signal forming means, a difference-frequency beat signal occurs. The intensity of the difference-frequency beat signal repeatedly becomes high and low at a frequency equal to the difference between the frequencies of the two laser beams.

In the manner described above, a plurality of kinds of difference-frequency beat signals occur such that the frequencies, at which the intensities of the difference-frequency beat signals repeatedly become high and low, may vary in accordance with the difference between the depths of the reflection planes from the inner surface of the sample.

The deep portion image signal output means discriminates a difference-frequency beat signal, the intensity of which repeatedly becomes high and low at a predetermined frequency, from the plurality of kinds of the difference-frequency beat signals occurring such that the frequencies, at which the intensities of the difference-frequency beat signals repeatedly become high and low, may vary. In this manner, a laser beam, which has been reflected from a reflection plane located at a predetermined depth in the sample, can be sorted out.

The intensity of the laser beam, which has been reflected from the reflection plane located at the specific depth in the sample, represents the information concerning the light reflection or light absorption at the deep portion of the sample, from which the laser beam has been reflected. Therefore, in the deep portion image signal output means, the deep portion image signal, which represents the form and/or structure of the portion located at the specific depth from the inner surface of the sample, can be generated from the difference-frequency beat signal, the intensity of which repeatedly becomes high and low at a predetermined frequency, and which has been discriminated in the manner described above.

Also, the irradiation of the laser beam to the sample may be repeated for at least two laser beams having different frequencies, which laser beams are produced by the laser beam source of the deep portion image output system utilizing the frequency-sweep optical heterodyne technique. In this manner, at least two discriminated difference-frequency beat signals are obtained. With the deep portion image signal output means, the values concerning constituents and/or functions of the portion, which is located at the predetermined depth from the inner surface of the sample, are calculated from at least two discriminated difference-frequency beat signals. The deep portion image signal representing the constituents and/or functions of the portion at the predetermined depth in the sample can then be obtained from the calculated values.

As described above, with the image composing endoscopes in accordance with the present invention, an image is composed from the deep portion image representing the form, the structure, the constituents and/or functions at a specific portion deep from the inner surface of the body cavity, which could not be visualized with the conventional endoscopes, and the visible surface image. The composed image is then displayed. Therefore, the state of the inner surface of the body cavity and the form, the structure, the constituents and/or functions at a specific portion deep from the inner surface of the body cavity, which could not be visualized with the conventional endoscopes, can be visualized in connection with each other. Accordingly, the image composing endoscopes in accordance with the present invention are advantageous in that diseased parts can be detected in their early stages.

BRIEF DESCRIPTION OF THE DRAWINGS

FIG. 12 is a block diagram showing a second embodiment of the image composing endoscope in accordance with the present invention, FIG. 13 is a block diagram showing a third embodiment of the image composing endoscope in accordance with the present invention.

DESCRIPTION OF THE PREFERRED EMBODIMENTS

The present invention will hereinbelow be described in further detail with reference to the accompanying drawings.

First, embodiments of the deep portion visualizing endoscope in accordance with the present invention will be described hereinbelow.

Figure 1:
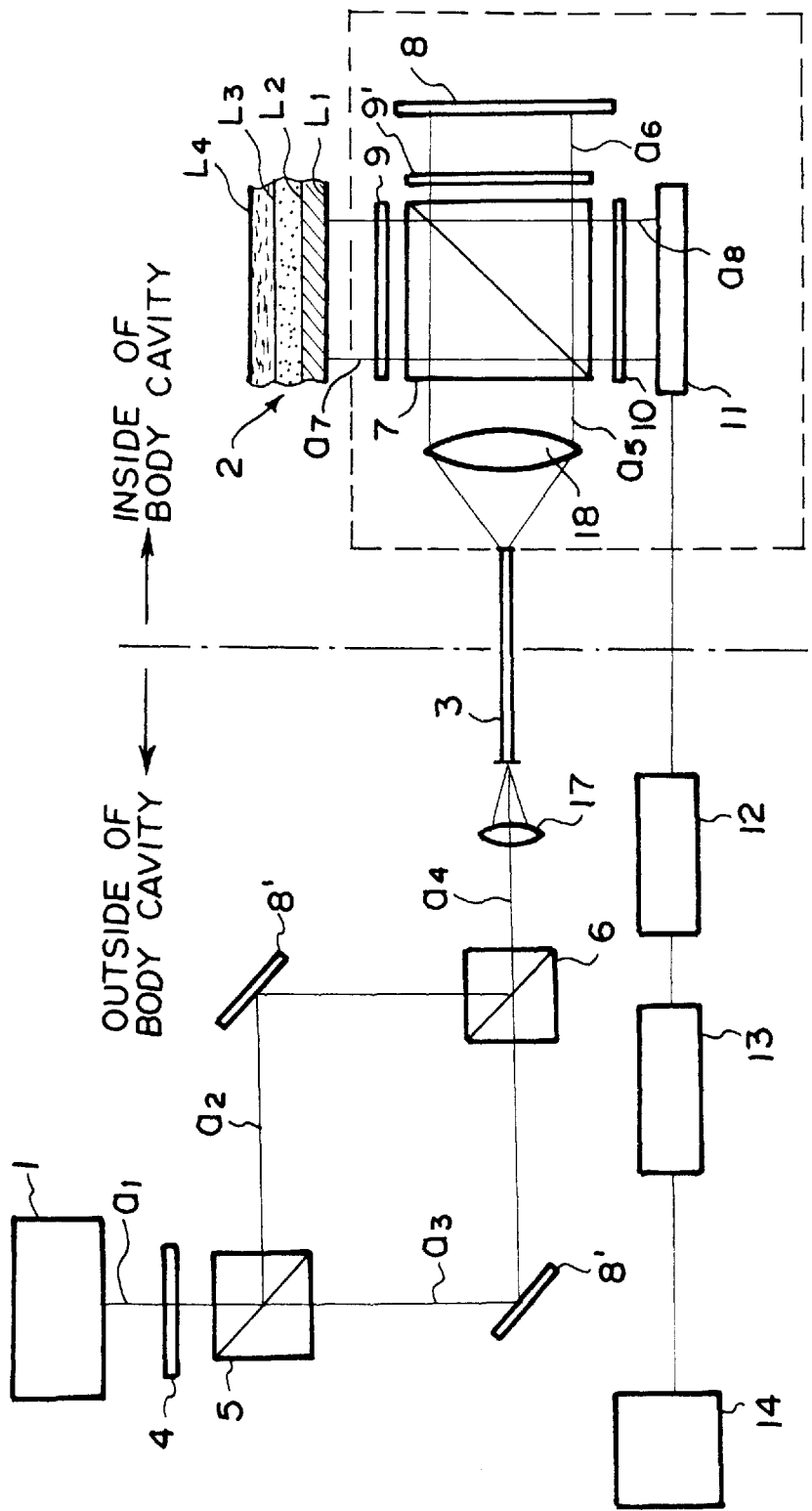
FIG. 1 is a block diagram showing a first embodiment of the deep portion visualizing endoscope in accordance with the present invention.

FIG. 1 is a block diagram showing a first embodiment of the deep portion visualizing endoscope in accordance with the present invention. This embodiment is provided with a frequency-sweep single frequency laser beam source 1 and a single mode fiber bundle 3. The single mode fiber bundle 3 has an entry end, from which a laser beam having been produced by the laser beam source 1 is entered, and a radiating end, from which the laser beam is radiated out and which is inserted into the body cavity. In FIG. 1, reference numeral 8' represents a mirror.

An optical path splitting means, which is constituted of a halfwave plate 4 and a polarization beam splitter 5, and a wavefront matching means constituted of a polarization beam splitter 6 are located between the laser beam source 1 and the single mode fiber bundle 3. The halfwave plate 4 and the polarization beam splitter 5 split a laser beam a1, which has been produced by the laser beam source 1, into two laser beams a2 and a3 having planes of polarization, which are approximately normal to each other. The polarization beam splitter 6 matches the wave fronts of the two laser beams a2 and a3 with each other on the same axis, and a wavefront-matched laser beam a4 is thereby obtained.

The laser beam a4 is guided through the single mode fiber bundle 3 and is guided as a laser beam a5 to a sample 2 in the body cavity. This embodiment is also provided with a second wavefront matching means, which is constituted of a polarization beam splitter 7 and two quarter-wave plates 9 and 9'. The second wavefront matching means splits the laser beam a5 into two laser beams a6 and a7 having planes of polarization, which are approximately normal to each other, and thereafter matches the wave fronts of the two laser beams a6 and a7 with each other. A mirror 8 is located in the optical path of the laser beam a6, which travels along one of the two optical paths having been split by the polarization beam splitter 7. The mirror 8 keeps the optical path length of the laser beam a6 at a predetermined length.

This embodiment is further provided with a polarizing plate 10 for transmitting the components of the two laser beams a6 and a7 having been subjected to the wavefront matching by the polarization beam splitter 7 and having the planes of polarization approximately normal to each other, which components have an identical direction of polarization. The polarizing plate 10 causes the components of the two laser beams a6 and a7, which components have an identical direction of polarization, to interfere with each other, and an interference laser beam a8 is thereby obtained. A parallel operation type of image sensor 11 detects a plurality of kinds of difference-frequency beat signals, which are formed by the interference laser beam a8.

This embodiment is still further provided with a parallel frequency analyzing means 12 for discriminating a difference-frequency beat signal, the intensity of which repeatedly becomes high and low at a predetermined frequency, from the plurality of kinds of the difference-frequency beat signals, which have been obtained from the parallel operation type of image sensor 11. A reconstruction means 13 reconstructs a plane image, or the like, of a portion located at a specific depth from the inner surface of the sample 2, from the intensity of the discriminated difference-frequency beat signal. Also, an image output means 14 outputs the reconstructed plane image, or the like, as a visible image.

How the first embodiment of the deep portion visualizing endoscope in accordance with the present invention operates will be described hereinbelow.

Figure 2:
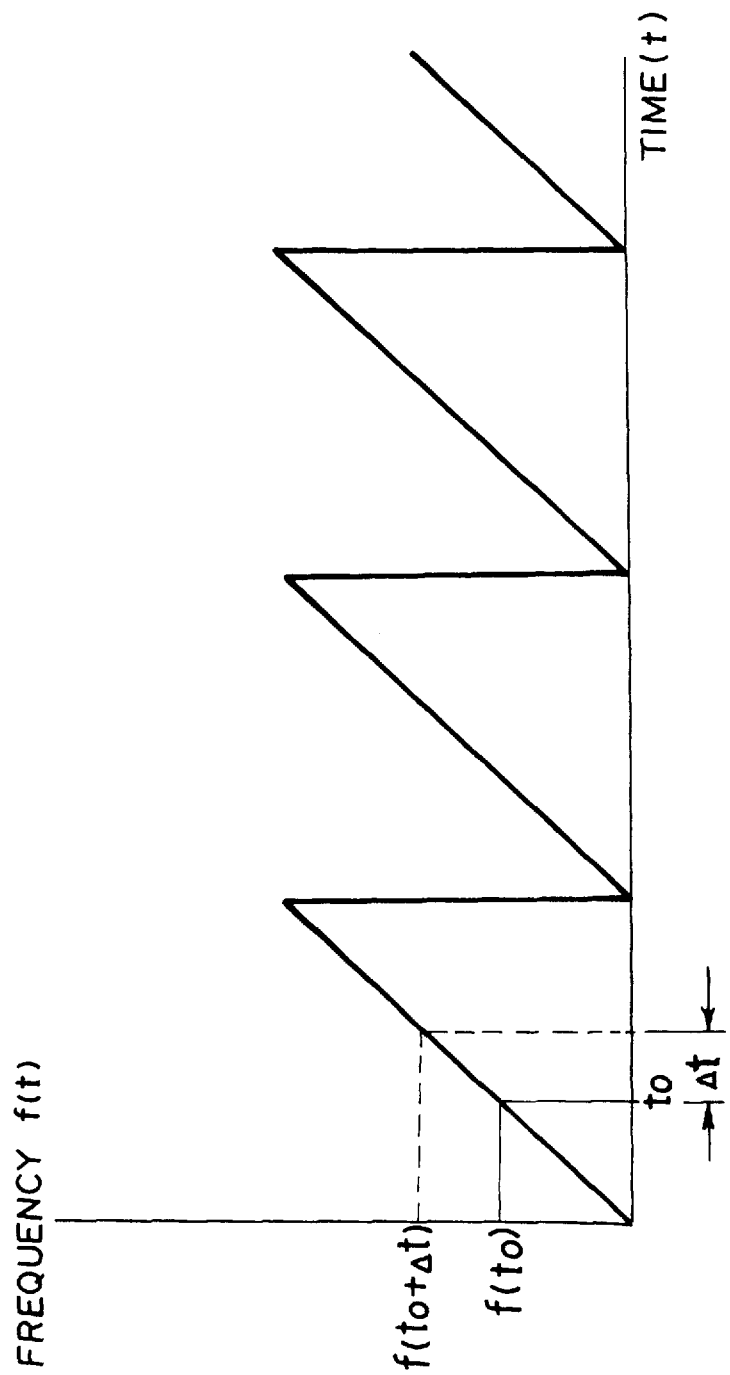
FIG. 2 is a graph showing a frequency-sweep wave form of a laser beam produced by a frequency-sweep single frequency laser beam source employed in embodiments of the deep portion visualizing endoscope in accordance with the present invention.

The laser beam source 1 produces the laser beam a1, the frequency of which is swept in the triangular wave form as shown in FIG. 2. The laser beam a1 is split by the halfwave plate 4 and the polarization beam splitter 5 into two laser beams a2 and a3 having the planes of polarization, which are approximately normal to each other. The laser beams a2 and a3 respectively travel along two split optical paths.

The wave fronts of the two split laser beams a2 and a3 are matched with each other by the polarization beam splitter 6. The wavefront-matched laser beam a4 is thereby obtained from the polarization beam splitter 6.

The wavefront-matched laser beam a4 is then passed through a lens 17 and entered into the single mode fiber bundle 3. The laser beam a4 is propagated inside of the single mode fiber bundle 3 and guided to the region inside of the body cavity.

The laser beam a4, which has been guided to the region inside of the body cavity, is collimated by a lens 18, and the collimated laser beam a5 is thereby obtained. The laser beam a5 is split by the polarization beam splitter 7 into the laser beam a7, which is irradiated to the sample 2, and the laser beam a6, which travels by the predetermined optical path length.

The laser beam a6, which travels by the predetermined optical path length, passes through a reflection surface of the polarization beam splitter 7 and the quarter-wave plate 9'. Thereafter, the laser beam a6 is reflected by the mirror 8, passes through the quarter-wave plate 9', and is then reflected by the reflection surface of the polarization beam splitter 7. At this time, while the laser beam a6 is traveling between the polarization beam splitter 7 and the mirror 8, the laser beam a6 passes two times through the quarter-wave plate 9'. Therefore, the plane of polarization of the laser beam a6 is rotated 90°, and the laser beam a6 is now reflected by the reflection surface of the polarization beam splitter 7.

The laser beam a7 having been irradiated to the sample 2 is reflected by a plurality of reflection planes L1, L2, L3, and L4 of the sample 2. The respective reflected laser beams travel to the polarization beam splitter 7.

At this time, the lengths of time occurring between when the laser beam a7 is radiated out of the polarization beam splitter 7 and when the laser beam a7 arrives at the polarization beam splitter 7 after being reflected from the reflection planes L1, L2, L3, and L4 vary in accordance with the depths of the reflection planes, which depths are taken from the inner surface of the sample 2.

The plurality of laser beams, which have been reflected from the reflection planes L1, L2, L3, and L4, are sequentially subjected by the polarization beam splitter 7 to the wavefront matching with the laser beam a6, which has traveled by the predetermined optical path length. The frequency of the laser beam a6, which has traveled by the predetermined optical path length and which is subjected to the wavefront matching with the plurality of the reflected laser beams, changes continuously in accordance with the frequency-sweep wave form shown in FIG. 2. At the time at which the wave front of the laser beam a6 is matched with the wave front of one of the reflected laser beams, the laser beam a6 has the frequency determined depending upon the depth of the reflection plane, from which the reflected laser beam was reflected, the depth being taken from the inner surface of the sample 2.

Each of laser beams, which have been sequentially obtained from the wavefront matching, passes through the polarizing plate 10. The polarizing plate 10 causes the components of the two laser beams subjected to the wavefront matching, which components have an identical direction of polarization, to interfere with each other. Therefore, a difference-frequency beat signal occurs. The intensity of the difference-frequency beat signal repeatedly becomes high and low at a frequency equal to the difference between the frequencies of the two laser beams subjected to the wavefront matching. In this manner, a plurality of kinds of difference-frequency beat signals occur such that the frequencies, at which the intensities of the difference-frequency beat signals repeatedly become high and low, may vary in accordance with the difference between the depths of the reflection planes L1, L2, L3, and L4, which depths are taken from the inner surface of the sample 2. The plurality of kinds of the difference-frequency beat signals are detected by the parallel operation type of image sensor 11. Also, a difference-frequency beat signal, the intensity of which repeatedly becomes high and low at a predetermined frequency, i.e. information representing the light absorption at the specific depth in the sample 2, is discriminated by the parallel frequency analyzing means 12 from the plurality of kinds of the difference-frequency beat signals. The reconstruction means 13 calculates the depth in the sample 2 from the frequency of the discriminated difference-frequency beat signal, the intensity of which repeatedly becomes high and low at the predetermined frequency. Also, the information representing the light absorption by the sample 2 is obtained from the intensity of the discriminated difference-frequency beat signal. A plane image of the portion located at the specific depth from the inner surface of the sample 2 is then reconstructed. Thereafter, the reconstructed plane image is fed out as a visible image from the image output means 14.

The discrimination of the difference-frequency beat signal, the intensity of which repeatedly becomes high and low at a predetermined frequency, from the plurality of kinds of the difference-frequency beat signals may be carried out for all of the plural kinds of frequencies by the parallel frequency analyzing means 12. The depths in the sample 2 and the corresponding information representing the light absorption may then be calculated by the reconstruction means 13. In this manner, a tomographic image at a site of the sample 2 to be viewed can be obtained.

Figure 3:
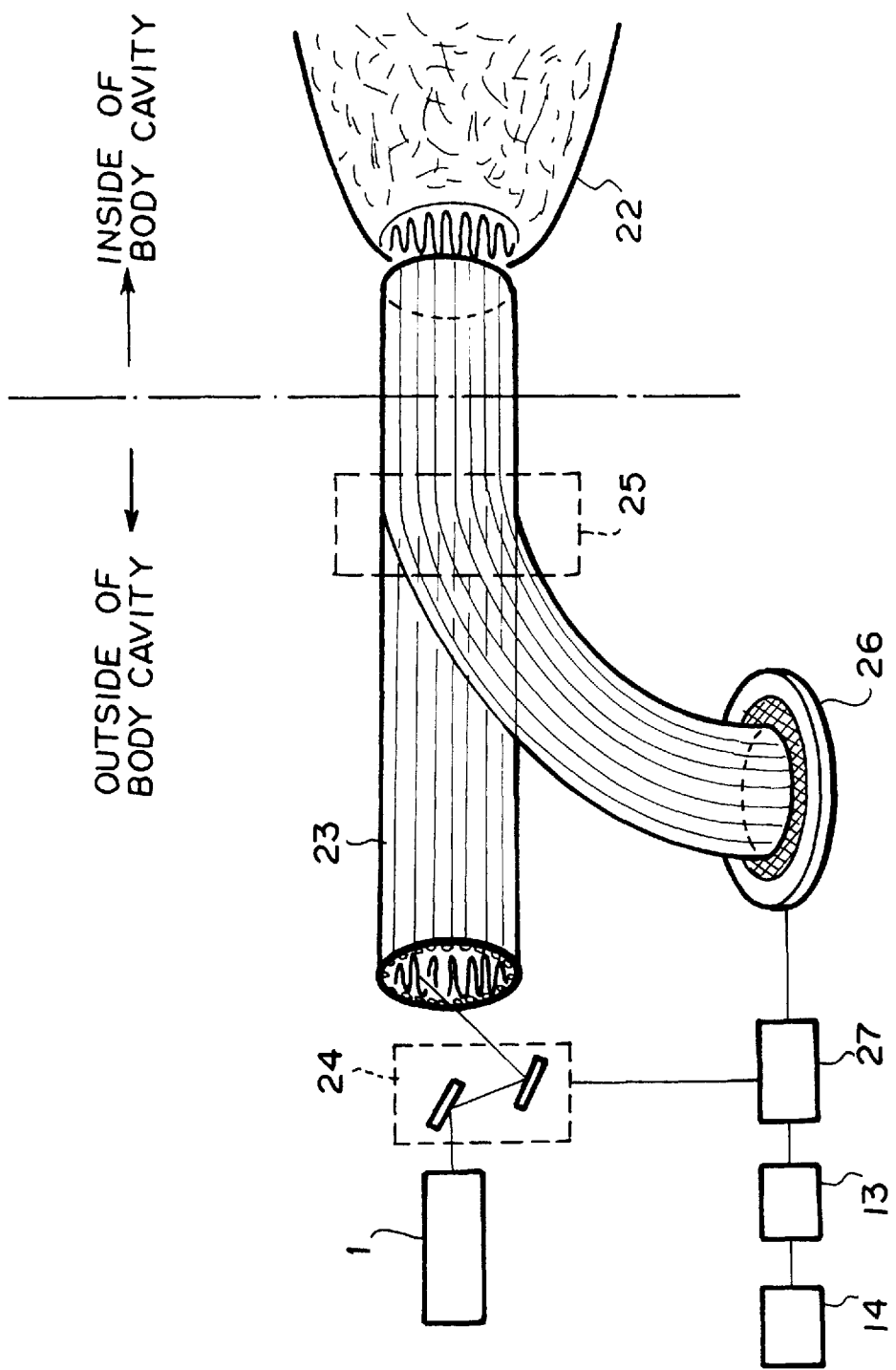
FIG. 3 is a block diagram showing a second embodiment of the deep portion visualizing endoscope in accordance with the present invention.

FIG. 3 is a block diagram showing a second embodiment of the deep portion visualizing endoscope in accordance with the present invention. This embodiment is provided with a frequency-sweep single frequency laser beam source 1 and a single mode image fiber bundle 23. The single mode image fiber bundle 23 has an entry end, from which a laser beam having been produced by the laser beam source 1 is entered, and a radiating end, from which the laser beam is radiated out and which is inserted into the body cavity.

A laser beam scanning means 24 is located between the laser beam source 1 and the single mode image fiber bundle 23. The scanning means 24 causes the laser beam, which has been produced by the laser beam source 1, to impinge sequentially upon entry ends of a plurality of image fibers constituting the image fiber bundle 23.

A fiber interference system 25 is located in order to split the laser beam having been entered into each of the image fibers of the image fiber bundle 23 from its entry end into a laser beam, which travels by a predetermined optical path length, and a laser beam, which is radiated out of the radiating end of the image fiber of the image fiber bundle 23. The fiber interference system 25 thereafter causes the laser beam, which has traveled by the predetermined optical path length, and the laser beam, which has been reflected by a sample 22 after being radiated out of the image fiber of the image fiber bundle 23 and which has then entered into the image fiber of the image fiber bundle 23 from the radiating end, to interfere with each other. An interference laser beam is thereby radiated out of the image fiber of the image fiber bundle 23.

This embodiment is also provided with an image sensor 26 for detecting a plurality of kinds of difference-frequency beat signals obtained from the interference in the fiber interference system 25 such that the frequencies, at which the intensities of the difference-frequency beat signals repeatedly become high and low, may vary.

This embodiment is further provided with a time series frequency analyzing means 27 for discriminating a difference-frequency beat signal, the intensity of which repeatedly becomes high and low at a predetermined frequency, from the plurality of kinds of the difference-frequency beat signals, which have been obtained from the image sensor 26. The reconstruction means 13 reconstructs an image of a portion, which is located at a specific depth from the surface of the sample 22, from the discriminated difference-frequency beat signal, the intensity of which repeatedly becomes high and low at the predetermined frequency. Also, the image output means 14 outputs the image, which has been reconstructed by the reconstruction means 13.

How the second embodiment of the deep portion visualizing endoscope in accordance with the present invention operates will be described hereinbelow.

The laser beam source 1 produces the laser beam, the frequency of which is swept in the triangular wave form as shown in FIG. 2. The laser beam, which has been produced by the laser beam source 1 is sequentially guided by the scanning means 24 to the entry ends of a plurality of fiber bundles, which constitute the image fiber bundle 23.

The laser beam, which has been guided to each fiber bundles constituting the image fiber bundle 23 travels inside of the fiber bundle and is split by the fiber interference system 25 into a laser beam, which travels by the predetermined optical path length, and a laser beam, which travels inside of the fiber bundle to its radiating end.

Figure 4:
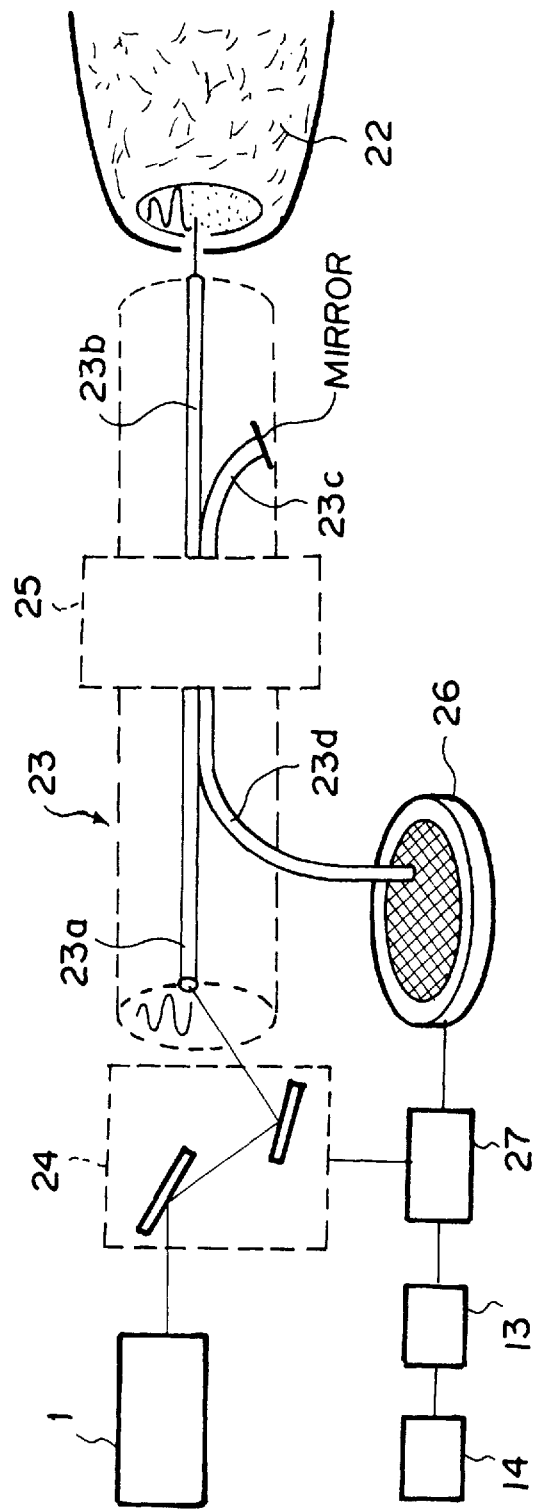
FIG. 4 is an explanatory view showing the second embodiment of the deep portion visualizing endoscope in accordance with the present invention.

FIG. 4 is an explanatory view showing one of the plurality of fiber bundles constituting the image fiber bundle 23, the view serving as an aid in facilitating the explanation of the operation of the second embodiment of the deep portion visualizing endoscope in accordance with the present invention.

Specifically, the laser beam is entered into a fiber bundle 23a by the scanning means 24. The laser beam is then split by the fiber interference system 25 constituted of a known optical coupler into two laser beams. One of the two split laser beams travels along an optical path (i.e. a fiber bundle 23b), which irradiates the sample 22. The other laser beam travels along an optical path (i.e. a fiber bundle 23c) having the predetermined optical path length.

The laser beam traveling along the optical path (i.e. the fiber bundle 23b), which irradiates the sample 22, is radiated out of the radiating end of the fiber bundle 23b and reflected by a plurality of reflection planes, which are located at the surface of the sample 22 and portions deep from the surface of the sample 22. A plurality of reflected laser beams, which have occurred in this manner, enter into the fiber bundle 23b from its radiating end and arrive at the fiber interference system 25.

On the other hand, the laser beam traveling along the optical path (i.e. the fiber bundle 23c) having the predetermined optical path length is reflected by a mirror and then arrives at the fiber interference system 25. The fiber interference system 25 causes the laser beam, which has thus arrived after traveling by the predetermined optical path length, and each of the plurality of the reflected laser beams, which have arrived after being reflected from the sample 22, to interfere with each other. At this time, the frequency of the laser beam, which has traveled along the optical path having the predetermined optical path length, changes continuously depending upon the difference between the lengths of time taken for the plurality of the reflected laser beams to arrive at the fiber interference system 25.

Therefore, when the respective reflected laser beams and the laser beam, which has traveled along the optical path having the predetermined optical path length, are caused to interfere with each other by the fiber interference system 25, a plurality of kinds of difference-frequency beat signals occur such that the frequencies, at which the intensities of the difference-frequency beat signals repeatedly become high and low, may vary. The plurality of kinds of the difference-frequency beat signals are guided through a fiber bundle 23d to the image sensor 26.

In the manner described above, the image sensor 26 detects the plurality of kinds of the difference-frequency beat signals in the order in which the scanning means 24 scans the fiber bundles of the image fiber bundle 23.

Thereafter, a difference-frequency beat signal, the intensity of which repeatedly becomes high and low at a predetermined frequency, is discriminated by the time series frequency analyzing means 27, which is synchronized with the scanning operation, from the plurality of kinds of the difference-frequency beat signals, which have been detected by the image sensor 26.

The reconstruction means 13 and the image output means 14 then operate in the same manner as that for the reconstruction means 13 and the image output means 14, which are employed in the embodiment of FIG. 1.

With the second embodiment of the deep portion visualizing endoscope in accordance with the present invention, in the manner described above, a plane image at an arbitrary depth in the sample 22 or a tomographic image of the sample 22 can be obtained.

Figure 5:
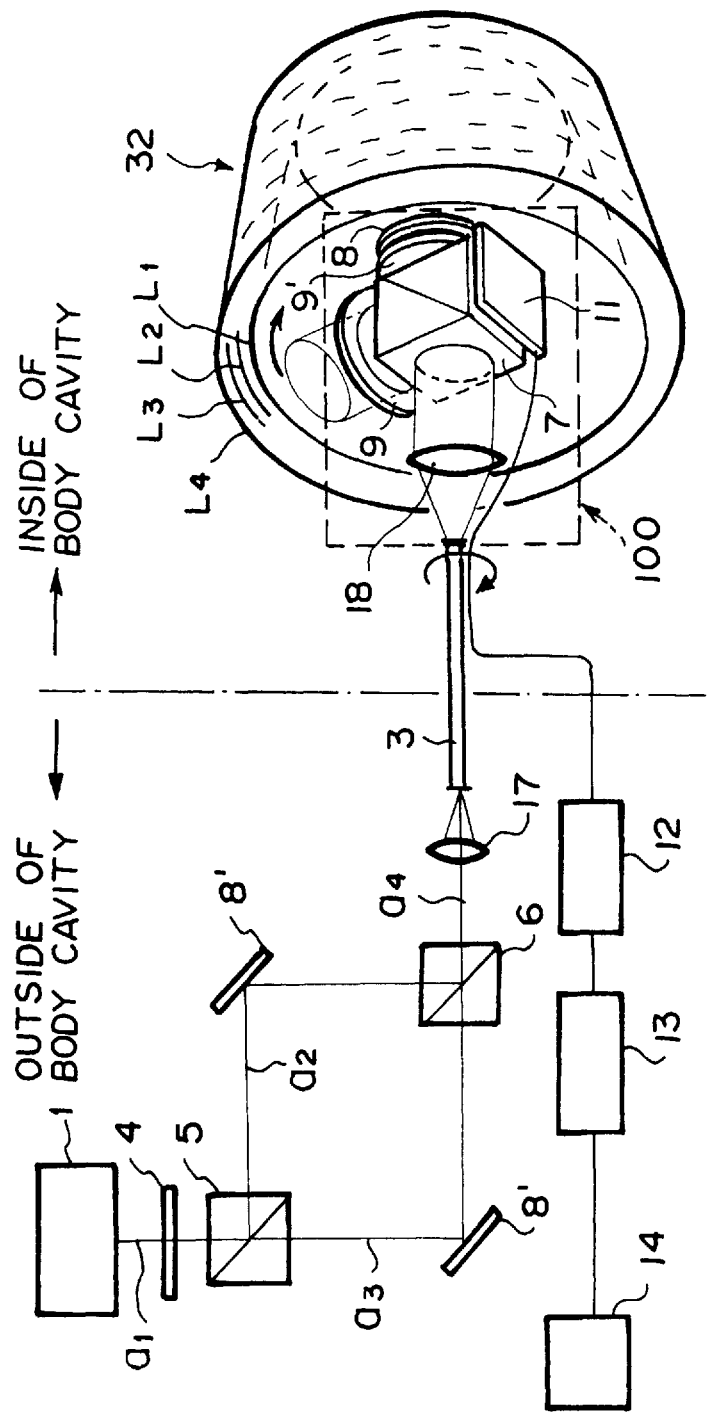
FIG. 5 is a block diagram showing a third embodiment of the deep portion visualizing endoscope in accordance with the present invention.

FIG. 5 is a block diagram showing a third embodiment of the deep portion visualizing endoscope in accordance with the present invention. This embodiment is identical with the first embodiment of FIG. 1, except that a rotation means 100 is provided. The rotation means 100 rotates the optical system, which comprises the polarization beam splitter 7, the quarter-wave plates 9 and 9', the mirror 8, the polarizing plate 10, the parallel operation type of image sensor 11, and the lens 18 and which is inserted into the body cavity, together around an axis, which is approximately parallel to the optical path of the laser beam having been radiated out of the radiating end of the single mode fiber bundle 3.

The third embodiment operates in the same manner as that for the first embodiment of FIG. 1 and has the same effects as those of the first embodiment. In addition, with the third embodiment, the rotation means 100 causes the laser beam to radially scan a tube cavity-like sample 32. Therefore, a tomographic image extending over the entire circumference of the sample 32 can be obtained.

Embodiments of the function diagnosing endoscope in accordance with the present invention will be described hereinbelow.

Figure 6:
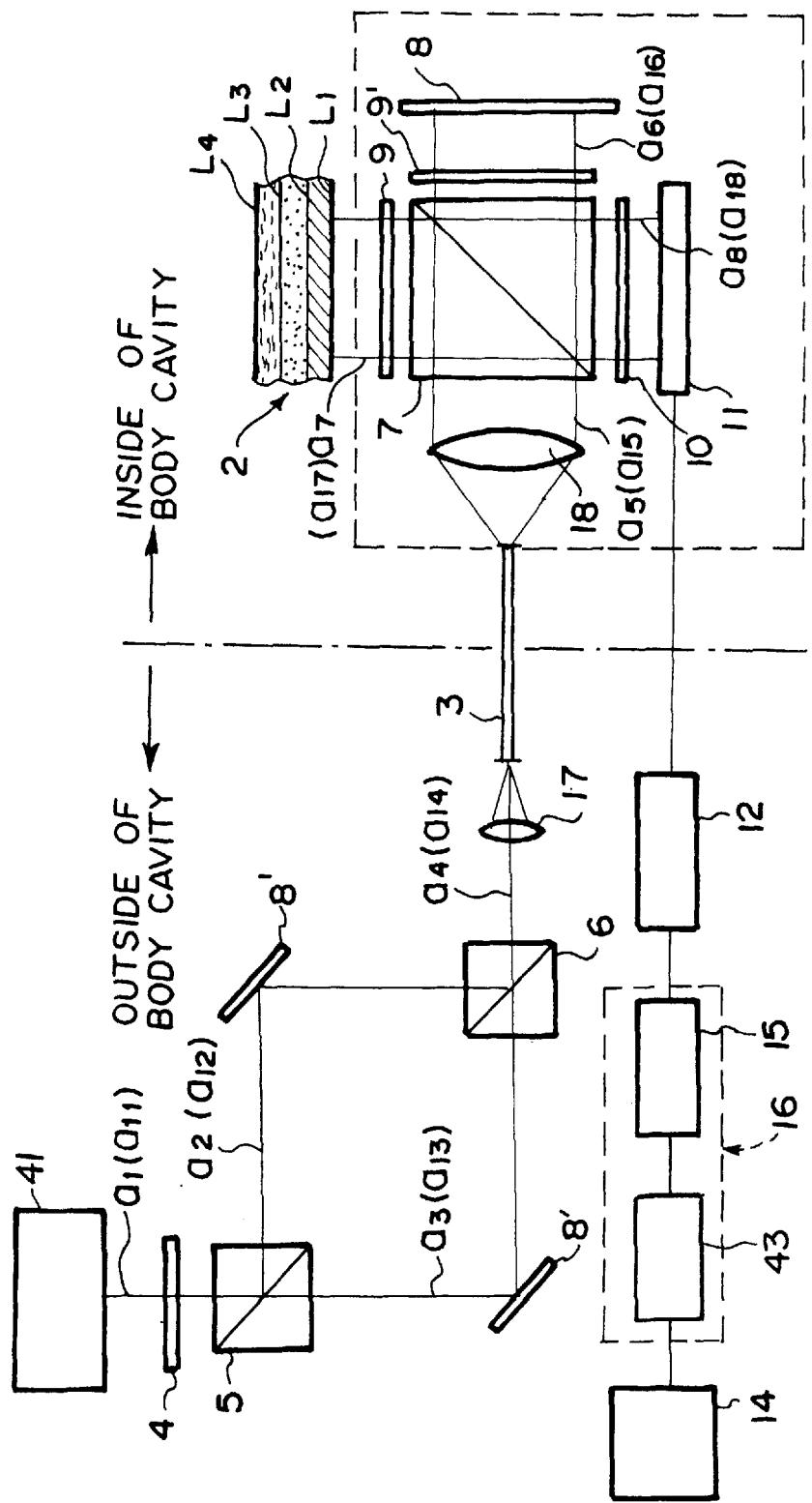
FIG. 6 is a block diagram showing a first embodiment of the function diagnosing endoscope in accordance with the present invention.

FIG. 6 is a block diagram showing a first embodiment of the function diagnosing endoscope in accordance with the present invention. In FIG. 6, similar elements are numbered with the same reference numerals with respect to FIG. 1. The structure of the first embodiment of the function diagnosing endoscope in accordance with the present invention is identical with the structure of the embodiment of FIG. 1, except that a laser beam source 41 capable of producing at least two laser beams having different frequencies such that the frequencies of the laser beams may be swept with the passage of time, is employed in lieu of the frequency-sweep single frequency laser beam source 1 employed in the embodiment of FIG. 1. Also, a calculation processing means 15 and a reconstruction means 43 are employed in lieu of the reconstruction means 13, which is employed in the embodiment of FIG. 1.

The calculation processing means 15 calculates values concerning constituents and/or functions of a portion, which is located at a specific depth from the inner surface of the sample 2, from at least two discriminated difference-frequency beat signals, the intensities of which repeatedly become high and low at predetermined frequencies and which are obtained when at least two laser beams having different frequencies are respectively irradiated to the sample 2. The reconstruction means 43 reconstructs a plane image, or the like, which represents constituents and/or functions of the portion located at the specific depth from the inner surface of the sample 2, from the calculated values.

This embodiment is also provided with the image output means 14 for feeding out the plane image, or the like, which has been reconstructed by the reconstruction means 43, as a visible image.

The reconstruction means 43 and the calculation processing means 15 together constitute a reconstructing section 16.

How the first embodiment of the function diagnosing endoscope in accordance with the present invention operates will be described hereinbelow.

Figure 7:
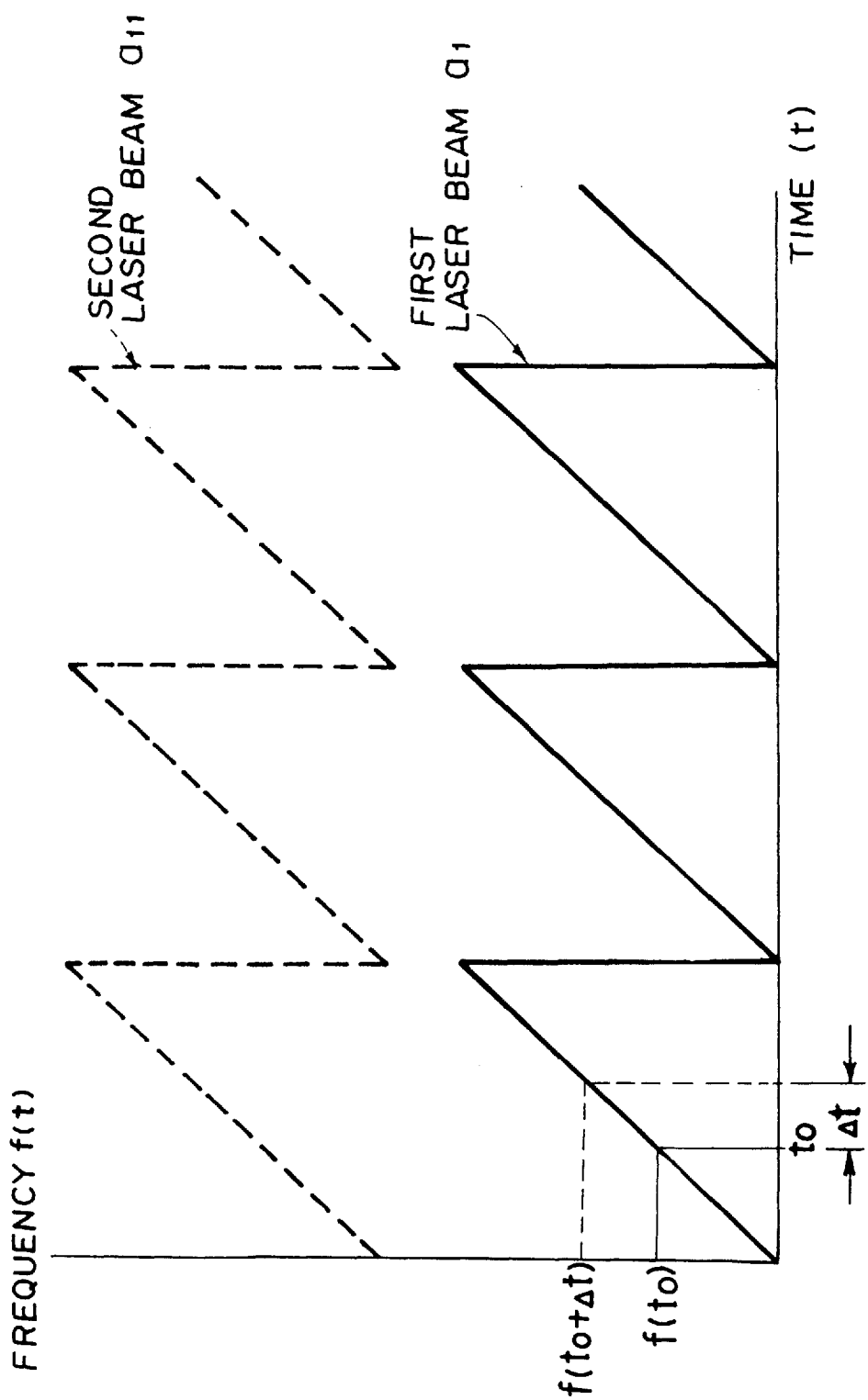
FIG. 7 is a graph showing frequency-sweep wave forms of laser beams produced by a frequency-sweep laser beam source employed in embodiments of the function diagnosing endoscope in accordance with the present invention.

The laser beam source 41 produces a first laser beam a1, the frequency of which is swept in the triangular wave form as indicated by the solid line in FIG. 7. The laser beam a1 is split by the halfwave plate 4 and the polarization beam splitter 5 into two laser beams a2 and a3 having the planes of polarization, which are approximately normal to each other. The laser beams a2 and a3 respectively travel along two split optical paths.

Thereafter, the same operations as those in the embodiment of FIG. 1 are carried out, and a difference-frequency beat signal, the intensity of which repeatedly becomes high and low at a predetermined frequency, i.e. information representing the light absorption at the specific depth in the sample 2, is discriminated by the parallel frequency analyzing means 12 from the plurality of kinds of the difference-frequency beat signals.

Thereafter, the laser beam source 41 produces a second laser beam a11 having a frequency band different from the frequency band of the first laser beam a1. The frequency of the second laser beam a11 is swept in the frequency-sweep wave form as indicated by the broken line in FIG. 7. In the same manner as that described above, a difference-frequency beat signal is discriminated which corresponds to the same depth in the sample 2 as the aforesaid specific depth associated with the difference-frequency beat signal that was obtained by irradiating the first laser beam a1 to the sample 2.

The calculation processing means 15 carries out calculation processing, such as calculation of the difference or the ratio, on the two discriminated difference-frequency beat signals, which are associated with the same depth in the sample 2. In this manner, information concerning the constituents and/or functions of the portion at the specific depth in the sample 2 is calculated from the difference between the intensities of light absorption with respect to the two frequency-sweep laser beams a1 and a11.

As an example of the information concerning the constituents and/or functions of the sample 2, information concerning the concentration of oxygen in the blood may be calculated. The concentration of oxygen in the blood is determined by the ratio between the concentrations of the oxidizing type of hemoglobin and the reducing type of hemoglobin, which constitute the blood. It has heretofore been known that the oxidizing type of hemoglobin characteristically absorbs light having a wavelength of 830 nm (nanometer), and the reducing type of hemoglobin characteristically absorbs light having a wavelength of 760 nm.

Therefore, in this embodiment, the frequency of the first laser beam a1 is swept in the region close to a wavelength of 830 nm, and the first laser beam a1 is irradiated to the sample 2. The concentration of the oxidizing type of hemoglobin is calculated from the information representing the light absorption by the oxidizing type of hemoglobin at the aforesaid specific depth in the sample 2. Also, the frequency of the second laser beam a11 is swept in the region close to a wavelength of 760 nm, and the second laser beam a11 is irradiated to the sample 2. In the same manner as that described above, the concentration of the reducing type of hemoglobin is calculated. The concentration of oxygen in the blood at the aforesaid specific depth in the sample 2 is calculated from the ratio between the concentrations of the two types of hemoglobin.

The information concerning the constituents and/or functions, which has been calculated in the manner described above, is reconstructed by the reconstruction means 43 as a plane image, or the like, of the portion located at the specific depth in the sample 2. Thereafter, the reconstructed plane image is fed out as a visible image from the image output means 14.

The discrimination of the difference-frequency beat signal, the intensity of which repeatedly becomes high and low at a predetermined frequency, from the plurality of kinds of the difference-frequency beat signals may be carried out for all of the plural kinds of frequencies by the parallel frequency analyzing means 12. Image reconstruction may then be carried out in the same manner as that described above from the discriminated difference-frequency beat signals, the intensities of which repeatedly become high and low at frequencies corresponding to the respective depths in the sample 2. In this manner, a tomographic image with respect to the depth direction of the sample 2 can be obtained.

Figure 8:
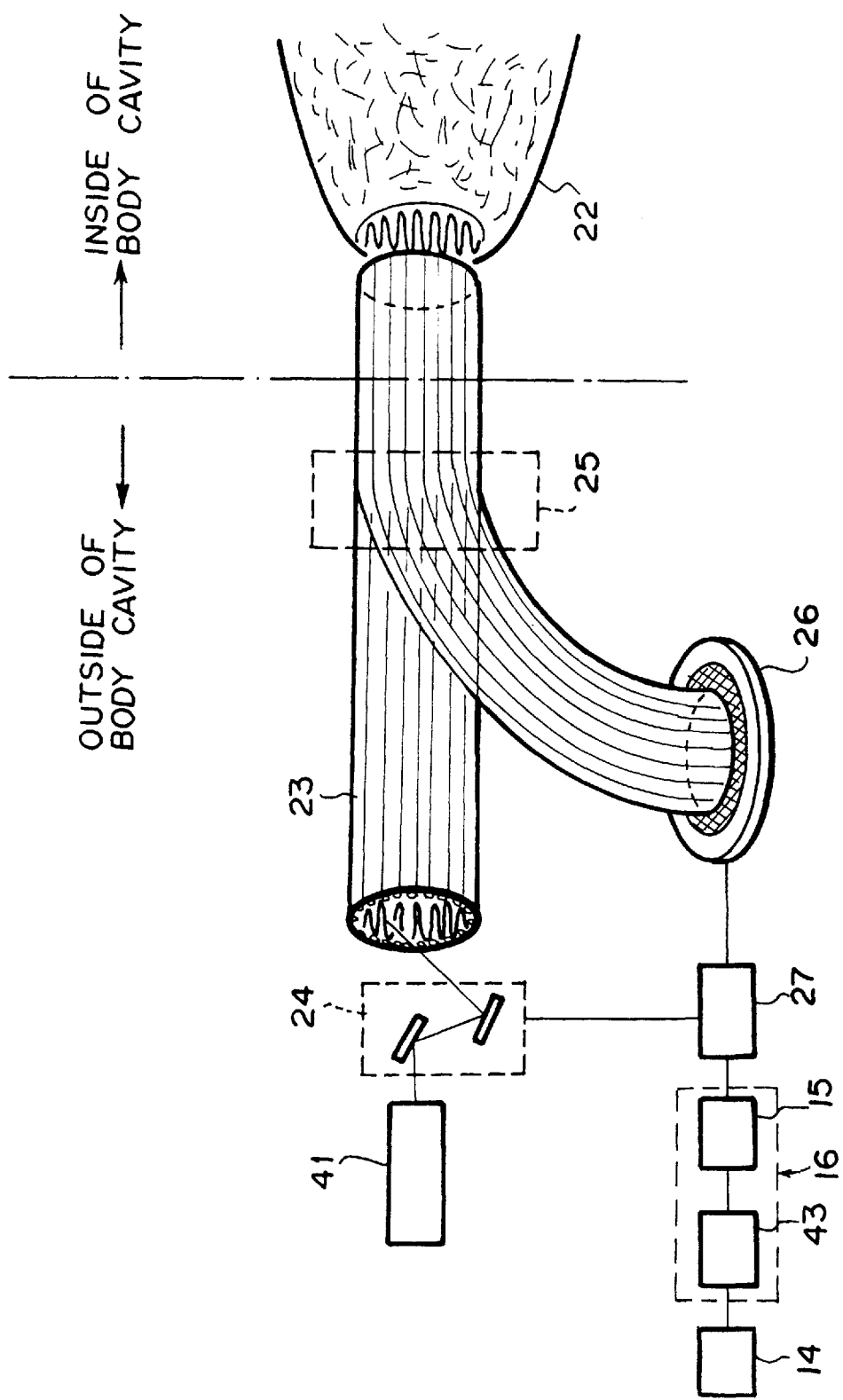
FIG. 8 is a block diagram showing a second embodiment of the function diagnosing endoscope in accordance with the present invention.

FIG. 8 is a block diagram showing a second embodiment of the function diagnosing endoscope in accordance with the present invention. In FIG. 8, similar elements are numbered with the same reference numerals with respect to FIG. 3. The structure of the second embodiment of the function diagnosing endoscope in accordance with the present invention is identical with the structure of the embodiment of FIG. 3, except that the laser beam source 41 capable of producing at least two laser beams having different frequencies such that the frequencies of the laser beams may be swept with the passage of time, is employed in lieu of the frequency-sweep single frequency laser beam source 1 employed in the embodiment of FIG. 3. Also, the calculation processing means 15 and the reconstruction means 43 are employed in lieu of the reconstruction means 13, which is employed in the embodiment of FIG. 3.

As in the first embodiment of the function diagnosing endoscope shown in FIG. 6, the calculation processing means 15 calculates values concerning constituents and/or functions of a portion, which is located at a specific depth from the surface of the sample 22, from at least two discriminated difference-frequency beat signals, the intensities of which repeatedly become high and low at predetermined frequencies and which are obtained when at least two laser beams having different frequencies are respectively irradiated to the sample 22. The reconstruction means 43 reconstructs a plane image, or the like, which represents constituents and/or functions of the portion located at the specific depth from the surface of the sample 22, from the calculated values. This embodiment is also provided with the image output means 14 for feeding out the plane image, or the like, which has been reconstructed by the reconstruction means 43, as a visible image.

Also, as in the first embodiment of the function diagnosing endoscope shown in FIG. 6, the reconstruction means 43 and the calculation processing means 15 together constitute the reconstructing section 16.

How the second embodiment of the function diagnosing endoscope in accordance with the present invention operates will be described hereinbelow.

The laser beam source 41 produces a first laser beam, the frequency of which is swept in the triangular wave form as indicated by the solid line in FIG. 7. The first laser beam, which has been produced by the laser beam source 41 is sequentially guided by the scanning means 24 to the entry ends of a plurality of fiber bundles, which constitute the image fiber bundle 23.

Thereafter, the same operations as those in the embodiment of FIG. 3 are carried out, and a difference-frequency beat signal, the intensity of which repeatedly becomes high and low at a predetermined frequency, is discriminated by the time series frequency analyzing means 27 from the plurality of kinds of the difference-frequency beat signals.

Thereafter, the laser beam source 41 produces a second laser beam having a frequency band different from the frequency band of the first laser beam. The frequency of the second laser beam is swept in the frequency-sweep wave form as indicated by the broken line in FIG. 7. In the same manner as that described above, a difference-frequency beat signal is discriminated which corresponds to the same depth in the sample 22 as the aforesaid specific depth associated with the difference-frequency beat signal that was obtained by irradiating the first laser beam to the sample 22.

Thereafter, in the same manner as that in the embodiment of FIG. 6, a plane image, a tomographic image, or the like, can be obtained which represents the constituents and/or functions at the specific depth in the sample 22.

Figure 9:
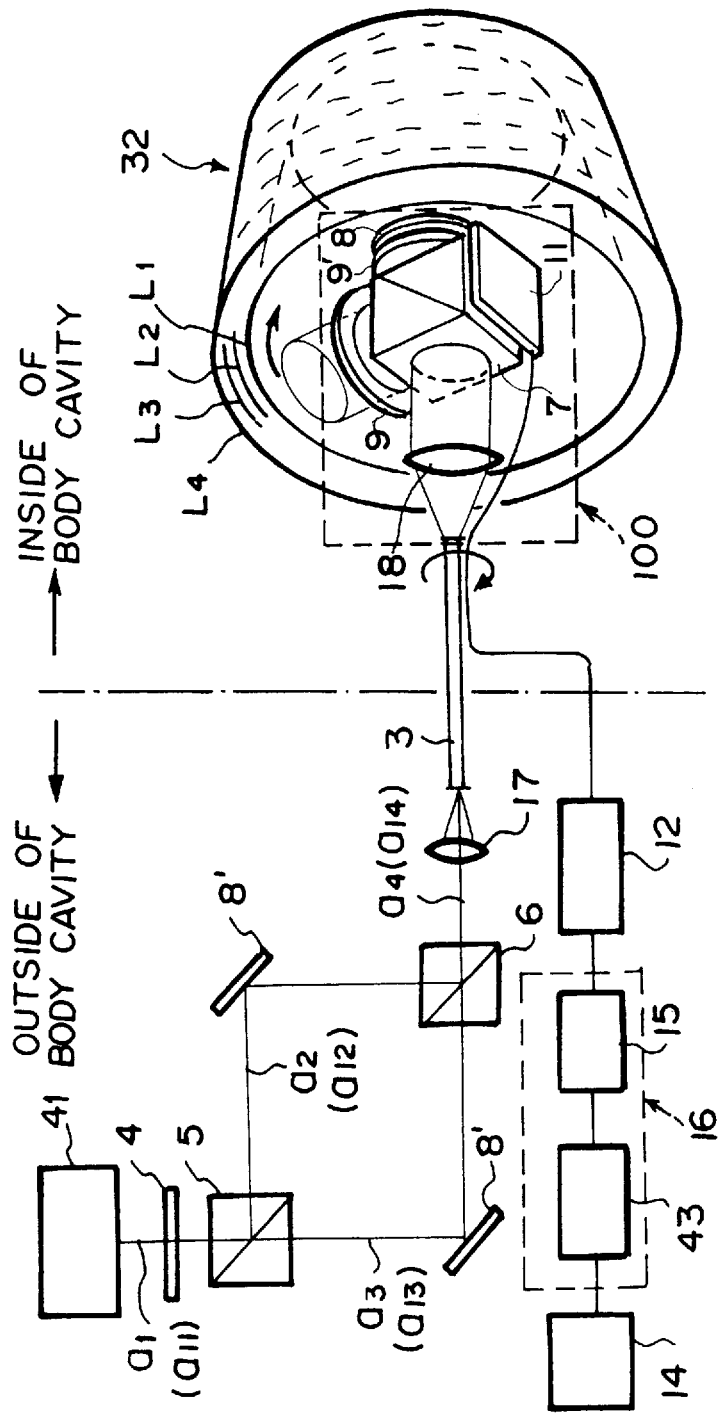
FIG. 9 is a block diagram showing a third embodiment of the function diagnosing endoscope in accordance with the present invention.

FIG. 9 is a block diagram showing a third embodiment of the function diagnosing endoscope in accordance with the present invention.

The third embodiment of the function diagnosing endoscope shown in FIG. 9 is identical with the embodiment of FIG. 6, except that a rotation means 100 is provided. The rotation means 100 rotates the optical system, which comprises the polarization beam splitter 7, the quarter-wave plates 9 and 9', the mirror 8, the polarizing plate 10, the parallel operation type of image sensor 11, and the lens 18 and which is inserted into the body cavity, together around an axis, which is approximately parallel to the optical path of the laser beam having been radiated out of the radiating end of the single mode fiber bundle 3.

The third embodiment of the function diagnosing endoscope shown in FIG. 9 operates in the same manner as that for the first embodiment of the function diagnosing endoscope shown in FIG. 6 and has the same effects as those of the embodiment of FIG. 6. In addition, with the third embodiment of the function diagnosing endoscope shown in FIG. 9, the rotation means 100 causes the laser beam to radially scan a tube cavity-like sample 32. Therefore, a tomographic image representing the constituents and/or functions at the entire circumference of the sample 32 can be obtained.

Embodiments of the image composing endoscope in accordance with the present invention will be described hereinbelow.

Figure 10:
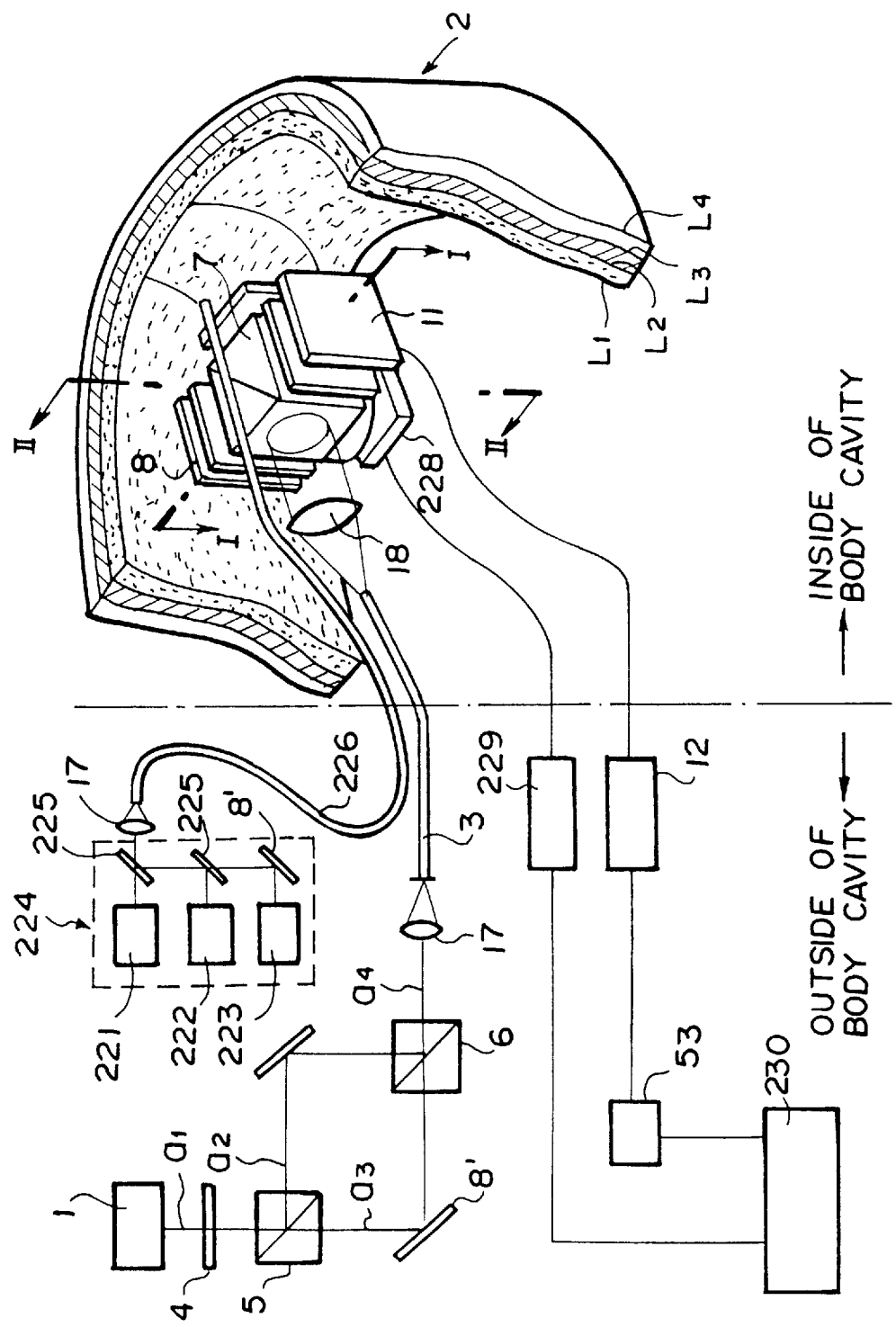
FIG. 10 is a block diagram showing a first embodiment of the image composing endoscope in accordance with the present invention.
Figure 11A:
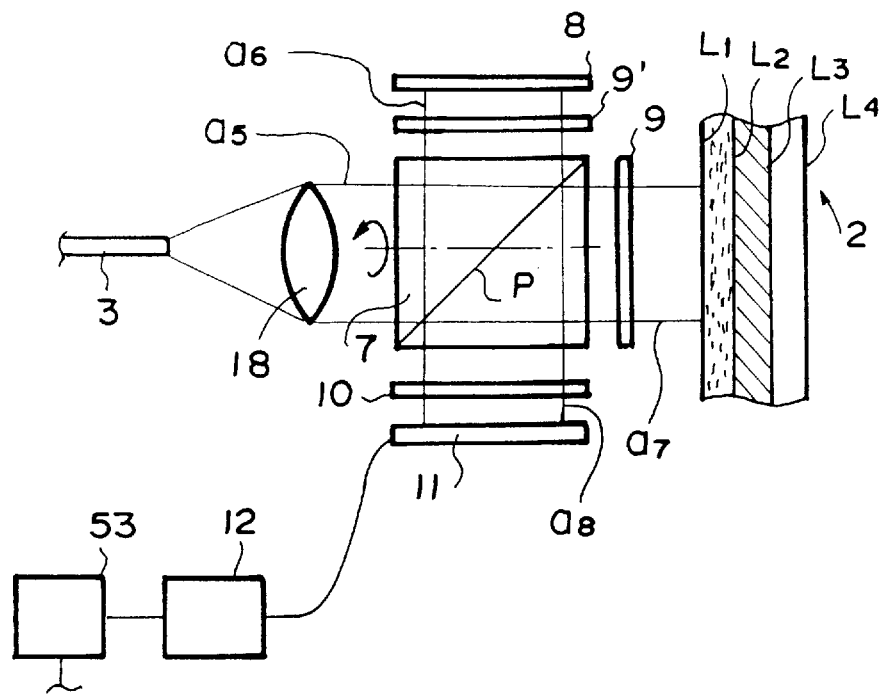
FIG. 11A is a sectional view taken along line I—I of FIG. 10.
Figure 11B:
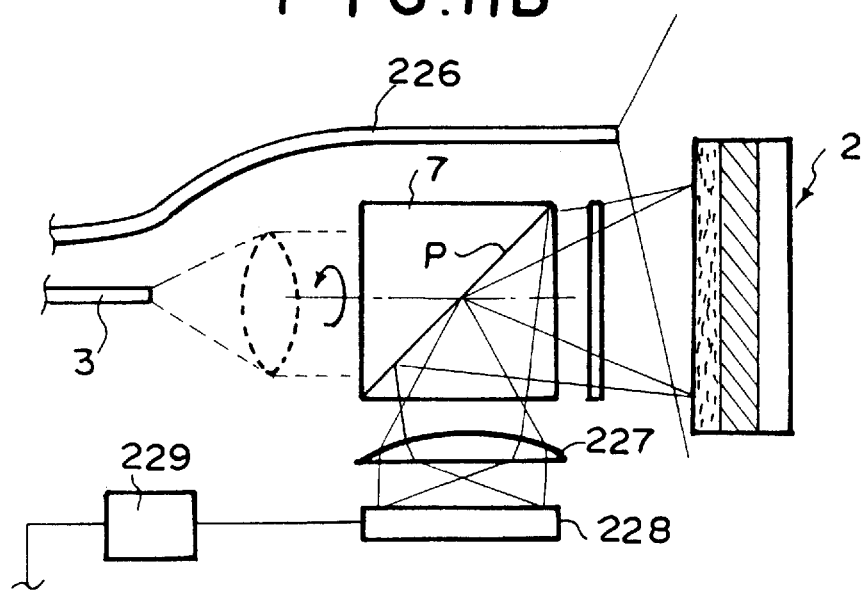
FIG. 11B is a sectional view taken along line II—II of FIG. 10.

FIG. 10 is a block diagram showing a first embodiment of the image composing endoscope in accordance with the present invention. FIG. 11A is a sectional view taken along line I—I of FIG. 10. FIG. 11B is a sectional view taken along line II—II of FIG. 10. In FIG. 10 and FIGS. 11A and 11B, similar elements are numbered with the same reference numerals with respect to FIG. 1. This embodiment comprises a deep portion image output system, a surface image output system, and an image composing and displaying means. First, how the deep portion image output system is constructed will be described hereinbelow.

In the deep portion image output system, the configuration of the region from the frequency-sweep single frequency laser beam source 1, which is capable of producing a laser beam having the frequency swept with the passage of time, to the lens 18 is identical with the configuration in the embodiment of FIG. 1.

As in the embodiment of FIG. 1, the laser beam a4 is guided through the single mode fiber bundle 3 (which serves as a first single mode fiber bundle 3 in this case) and is guided as the laser beam a5 to the sample 2 in the body cavity. The deep portion image output system is also provided with a second wavefront matching means, which is constituted of a polarization beam splitter 7 and two quarter-wave plates 9 and 9'. The second wavefront matching means splits the laser beam a5 into two laser beams a6 and a7 having planes of polarization, which are approximately normal to each other, and thereafter matches the wave fronts of the two laser beams a6 and a7 with each other. A mirror 8 is located in the optical path of the laser beam a6, which travels along one of the two optical paths having been split by the polarization beam splitter 7. The mirror 8 keeps the optical path length of the laser beam a6 at a predetermined length. In this embodiment, the polarization beam splitter 7 can rotate around an axis parallel to the direction, along which the laser beam a5 having been radiated out of the radiating end of the first single mode fiber bundle 3 travels.

The deep portion image output system is further provided with a polarizing plate 10 for transmitting the components of the two laser beams a6 and a7 having been subjected to the wavefront matching by the polarization beam splitter 7 and having the planes of polarization approximately normal to each other, which components have an identical direction of polarization. The polarizing plate 10 causes the components of the two laser beams a6 and a7, which components have an identical direction of polarization, to interfere with each other, and an interference laser beam a8 is thereby obtained. A parallel operation type of image sensor 11 detects a plurality of kinds of difference-frequency beat signals, which are formed by the interference laser beam a8.

The deep portion image output system is still further provided with a parallel frequency analyzing means 12 for discriminating a difference-frequency beat signal, the intensity of which repeatedly becomes high and low at a predetermined frequency, from the plurality of kinds of the difference-frequency beat signals, which have been obtained from the parallel operation type of image sensor 11. A reconstruction means 53 generates a deep portion image signal, which represents the form and/or structure of a portion located at a specific depth from the inner surface of the sample 2, from the discriminated difference-frequency beat signal, the intensity of which repeatedly becomes high and low at the predetermined frequency.

How the surface image output system is constructed will be described hereinbelow.

The surface image output system is provided with an RGB laser beam source 224, which comprises a red laser beam source 221, a green laser beam source 222, and a blue laser beam source 223. Laser beams produced by the red laser beam source 221, the green laser beam source 222, and the blue laser beam source 223 are combined with one another by a mirror 8' and dichroic mirrors 225, 225, and an RGB laser beam is thereby obtained.

The surface image output system is also provided with a second single mode fiber bundle 226 having an entry end, from which the RGB laser beam having been produced by the RGB laser beam source 224 is entered via a lens 17, and a radiating end, which is inserted into the body cavity and from which the RGB laser beam is radiated out. The surface image output system is further provided with a lens 227. The lens 227 forms an image of the laser beam, which has been reflected from the inner surface of the sample 2 after being radiated out of the radiating end of the second single mode fiber bundle 226. A CCD image sensor 228 detects the surface image, which has been formed by the lens 227. Also, a video processor 229 generates a surface image output signal from the detected surface image.

The first embodiment of the image composing endoscope shown in FIG. 10 is further provided with a cathode-ray tube (CRT) display device 230, which composes an image from the deep portion image signal representing the deep portion image and the surface image signal representing the surface image, and which displays the composed image.

How the first embodiment of the image composing endoscope in accordance with the present invention operates will be described hereinbelow.

First, how the deep portion image output system operates will be described hereinbelow.

As in the embodiment of FIG. 1, the frequency-sweep single frequency laser beam source 1 produces the laser beam a1, the frequency of which is swept in the triangular wave form as shown in FIG. 2. The laser beam a1 is split by the halfwave plate 4 and the polarization beam splitter 5 into two laser beams a2 and a3 having the planes of polarization, which are approximately normal to each other. The laser beams a2 and a3 respectively travel along two split optical paths.

The wave fronts of the two split laser beams a2 and a3 are matched with each other by the polarization beam splitter 6. The wavefront-matched laser beam a4 is thereby obtained from the polarization beam splitter 6.

The wavefront-matched laser beam a4 is then passed through the corresponding lens 17 and entered into the first single mode fiber bundle 3. The laser beam a4 is propagated inside of the first single mode fiber bundle 3 and guided to the region inside of the body cavity.

The laser beam a4, which has been guided to the region inside of the body cavity, is collimated by the lens 18, and the collimated laser beam a5 is thereby obtained. The laser beam a5 is split by the polarization beam splitter 7 into the laser beam a7, which is irradiated to the sample 2, and the laser beam a6, which travels by the predetermined optical path length.

The laser beam a6, which travels by the predetermined optical path length, is reflected by a reflection surface P of the polarization beam splitter 7 and passes through the quarter-wave plate 9'. Thereafter, the laser beam a6 is reflected by the mirror 8, passes through the quarter-wave plate 9', and then passes through the reflection surface P of the polarization beam splitter 7.

The laser beam a7 having been irradiated to the sample 2 is reflected by a plurality of reflection planes L1, L2, L3, and L4 of the sample 2. The respective reflected laser beams travel to the polarization beam splitter 7.

The plurality of laser beams, which have been reflected from the reflection planes L1, L2, L3, and L4, are sequentially subjected by the polarization beam splitter 7 to the wavefront matching with the laser beam a6, which has traveled by the predetermined optical path length. The frequency of the laser beam a6, which has traveled by the predetermined optical path length and which is subjected to the wavefront matching with the plurality of the reflected laser beams, changes continuously in accordance with the frequency-sweep wave form shown in FIG. 2. At the time at which the wave front of the laser beam a6 is matched with the wave front of one of the reflected laser beams, the laser beam a6 has the frequency determined depending upon the depth of the reflection plane, from which the reflected laser beam was reflected, the depth being taken from the inner surface of the sample 2.

Specifically, as shown in FIG. 2, at a certain instant t0, the laser beam having a frequency of f(t0) is produced by the laser beam source 1. A difference of $\Delta t$ will occur between the length of time required for the laser beam, which is irradiated to the sample 2, to return to the polarization beam splitter 7 and the length of time required for the laser beam, which travels by the predetermined optical path length, to return to the polarization beam splitter 7. In such cases, the laser beam, which has traveled by the predetermined optical path length and which is subjected by the polarization beam splitter 7 to the wavefront matching with the laser beam, which has been irradiated to the sample 2 and which the frequency f(t0), will have a frequency of f(t0+$\Delta t$).

Each of laser beams, which have been sequentially obtained from the wavefront matching in the manner described above, passes through the polarizing plate 10. The polarizing plate 10 causes the components of the two laser beams subjected to the wavefront matching, which components have an identical direction of polarization, to interfere with each other. Therefore, a difference-frequency beat signal occurs. The intensity of the difference-frequency beat signal repeatedly becomes high and low at a frequency equal to the difference between the frequencies of the two laser beams subjected to the wavefront matching. In this manner, a plurality of kinds of difference-frequency beat signals occur such that the frequencies, at which the intensities of the difference-frequency beat signals repeatedly become high and low, may vary in accordance with the difference between the depths of the reflection planes L1, L2, L3, and L4, which depths are taken from the inner surface of the sample 2.

The plurality of kinds of the difference-frequency beat signals are detected by the parallel operation type of image sensor 11. Also, a difference-frequency beat signal, the intensity of which repeatedly becomes high and low at a predetermined frequency, i.e. information representing the light absorption at the specific depth in the sample 2, is discriminated by the parallel frequency analyzing means 12 from the plurality of kinds of the difference-frequency beat signals.

The reconstruction means 53 generates the deep portion image signal, which represents the form and/or structure of the portion located at the specific depth from the inner surface of the sample 2, from the light absorption information, which has been discriminated in the manner described above.

How the surface image output system operates will be described hereinbelow.

The RGB laser beam is produced by the RGB laser beam source 224 and is entered via the lens 17 into the second single mode fiber bundle 226. The RGB laser beam is then propagated inside of the fiber bundle 226, guided to the region inside of the body cavity, and is irradiated to the inner surface of the sample 2.

At this time, the polarization beam splitter 7 is rotated, and the direction of the reflection surface P of the polarization beam splitter 7 is rotated 90°. As illustrated in FIG. 11B, the RGB laser beam, which has been irradiated to the inner surface of the sample 2 and has then been reflected therefrom, is reflected by the reflection surface P of the polarization beam splitter 7, which has thus been rotated. An image of the RGB laser beam is then formed by the lens 227 and is detected by the CCD image sensor 228.

The video processor 229 generates the surface image signal from the detected laser beam, i.e. from the surface image of the sample 2.

The CRT display device 230 composes an image from the deep portion image signal, which represents the form and/or structure at the deep portion in the sample 2 and which has been obtained from the deep portion image output system, and the surface image signal, which has been obtained from the surface image output system. The image, which has thus been composed of the surface image of the sample 2 and the deep portion image representing the form and/or structure at the deep portion in the sample 2, is displayed on the CRT display device 230.

FIG. 12 is a block diagram showing a second embodiment of the image composing endoscope in accordance with the present invention. In FIG. 12, similar elements are numbered with the same reference numerals with respect to FIG. 3.

The second embodiment of the image composing endoscope shown in FIG. 12 comprises a deep portion image output system, a surface image output system, and the CRT display device 230 serving as an image composing and displaying means. The structures of the surface image output system and the CRT display device 230 are the same as those in the first embodiment of the image composing endoscope shown in FIG. 10. Therefore, how the deep portion image output system is constructed will be described hereinbelow.

In the deep portion image output system in the embodiment of FIG. 10, the configuration of the region from the frequency-sweep single frequency laser beam source 1, which is capable of producing a laser beam having the frequency swept with the passage of time, to the time series frequency analyzing means 27 is identical with the configuration employed in the embodiment of FIG. 3.

As described above, the time series frequency analyzing means 27 discriminates a difference-frequency beat signal, the intensity of which repeatedly becomes high and low at a predetermined frequency, from the plurality of kinds of the difference-frequency beat signals. As in the embodiment of FIG. 10, the reconstruction means 53 generates a deep portion image signal, which represents the form and/or structure of a portion located at a specific depth from the inner surface of the sample 22, from the discriminated difference-frequency beat signal, the intensity of which repeatedly becomes high and low at the predetermined frequency.

How the second embodiment of the image composing endoscope shown in FIG. 12 operates will be described hereinbelow.

The laser beam source 1 produces the laser beam, the frequency of which is swept in the triangular wave form as shown in FIG. 2. The laser beam, which has been produced by the laser beam source 1 is sequentially guided by the scanning means 24 to the entry ends of a plurality of fiber bundles, which constitute the image fiber bundle 23.

Thereafter, the same operations as those in the embodiment of FIG. 3 are carried out, and the image sensor 26 two-dimensionally detects the plurality of kinds of the difference-frequency beat signals in the order in which the scanning means 24 scans the fiber bundles of the image fiber bundle 23.

Thereafter, a difference-frequency beat signal, the intensity of which repeatedly becomes high and low at a predetermined frequency, is discriminated by the time series frequency analyzing means 27, which is synchronized with the scanning operation, from the plurality of kinds of the difference-frequency beat signals, which have been detected by the image sensor 26.

Thereafter, in the same manner as that in the embodiment of FIG. 10, the deep portion image signal representing the form and/or structure at the specific depth in the sample 22 is generated.

The surface image output system and the CRT display device 230 operate in the same manner as those in the embodiment of FIG. 10. An image is composed from the surface image of the sample 22 and the deep portion image representing the form and/or structure at the specific depth in the sample 22. The composed image is displayed on the CRT display device 230.

FIG. 13 is a block diagram showing a third embodiment of the image composing endoscope in accordance with the present invention. In FIG. 13, similar elements are numbered with the same reference numerals with respect to FIG. 10. The structure of the third embodiment of the image composing endoscope in accordance with the present invention is identical with the structure of the embodiment of FIG. 10, except that a laser beam source 41 capable of producing at least two laser beams having different frequencies such that the frequencies of the laser beams may be swept with the passage of time, is employed in lieu of the frequency-sweep single frequency laser beam source 1 employed in the embodiment of FIG. 10. Also, a calculation processing means 15 and a reconstruction means 59 are employed in lieu of the reconstruction means 53, which is employed in the embodiment of FIG. 10.

The calculation processing means 15 calculates values concerning constituents and/or functions of a portion, which is located at a specific depth from the inner surface of the sample 2, from at least two discriminated difference-frequency beat signals, the intensities of which repeatedly become high and low at predetermined frequencies and which are obtained when at least two laser beams having different frequencies and having been produced by the frequency-sweep laser beam source 41 are respectively irradiated to the sample 2. The reconstruction means 59 generates a deep portion image signal, which represents constituents and/or functions of the portion located at the specific depth from the inner surface of the sample 2, from the calculated values.

The reconstruction means 59 and the calculation processing means 15 together constitute a reconstructing section 56.

How the third embodiment of the image composing endoscope in accordance with the present invention operates will be described hereinbelow.

The frequency-sweep laser beam source 41 produces a first laser beam a1, the frequency of which is swept in the triangular wave form as indicated by the solid line in FIG. 7. The laser beam a1 is split by the halfwave plate 4 and the polarization beam splitter 5 into two laser beams a2 and a3 having the planes of polarization, which are approximately normal to each other. The laser beams a2 and a3 respectively travel along two split optical paths.

Thereafter, the same operations as those in the embodiment of FIG. 10 are carried out, and a difference-frequency beat signal, the intensity of which repeatedly becomes high and low at a predetermined frequency, i.e. information representing the light absorption at the specific depth in the sample 2, is discriminated by the parallel frequency analyzing means 12 from the plurality of kinds of the difference-frequency beat signals.

Thereafter, the laser beam source 41 produces a second laser beam a11 having a frequency band different from the frequency band of the first laser beam a1. The frequency of the second laser beam a11 is swept in the frequency-sweep wave form as indicated by the broken line in FIG. 7. In the same manner as that described above, a difference-frequency beat signal is discriminated which corresponds to the same depth in the sample 2 as the aforesaid specific depth associated with the difference-frequency beat signal that was obtained by irradiating the first laser beam a1 to the sample 2.

The calculation processing means 15 carries out calculation processing, such as calculation of the difference or the ratio, on the two discriminated difference-frequency beat signals, which are associated with the same depth in the sample 2. In this manner, information concerning the constituents and/or functions of the portion at the specific depth in the sample 2, e.g. the concentration of oxygen in the blood, is calculated from the difference between the intensities of light absorption with respect to the two frequency-sweep laser beams a1 and a11.

The deep portion image signal, which represents constituents and/or functions of the portion located at the specific depth from the inner surface of the sample 2, is generated by the reconstruction means 59 from the information concerning the constituents and/or functions, which has been calculated in the manner described above.

The surface image output system operates in the same manner as that for the surface image output system, which is employed in the embodiment of FIG. 10.

Thereafter, the CRT display device 230 composes an image from the deep portion image signal, which has been obtained from the deep portion image output system, and the surface image signal, which has been obtained from the surface image output system. The image, which has thus been composed of the surface image of the sample 2 and the deep portion image representing the constituents and/or functions at the deep portion in the sample 2, is displayed on the CRT display device 230.

Figure 14:
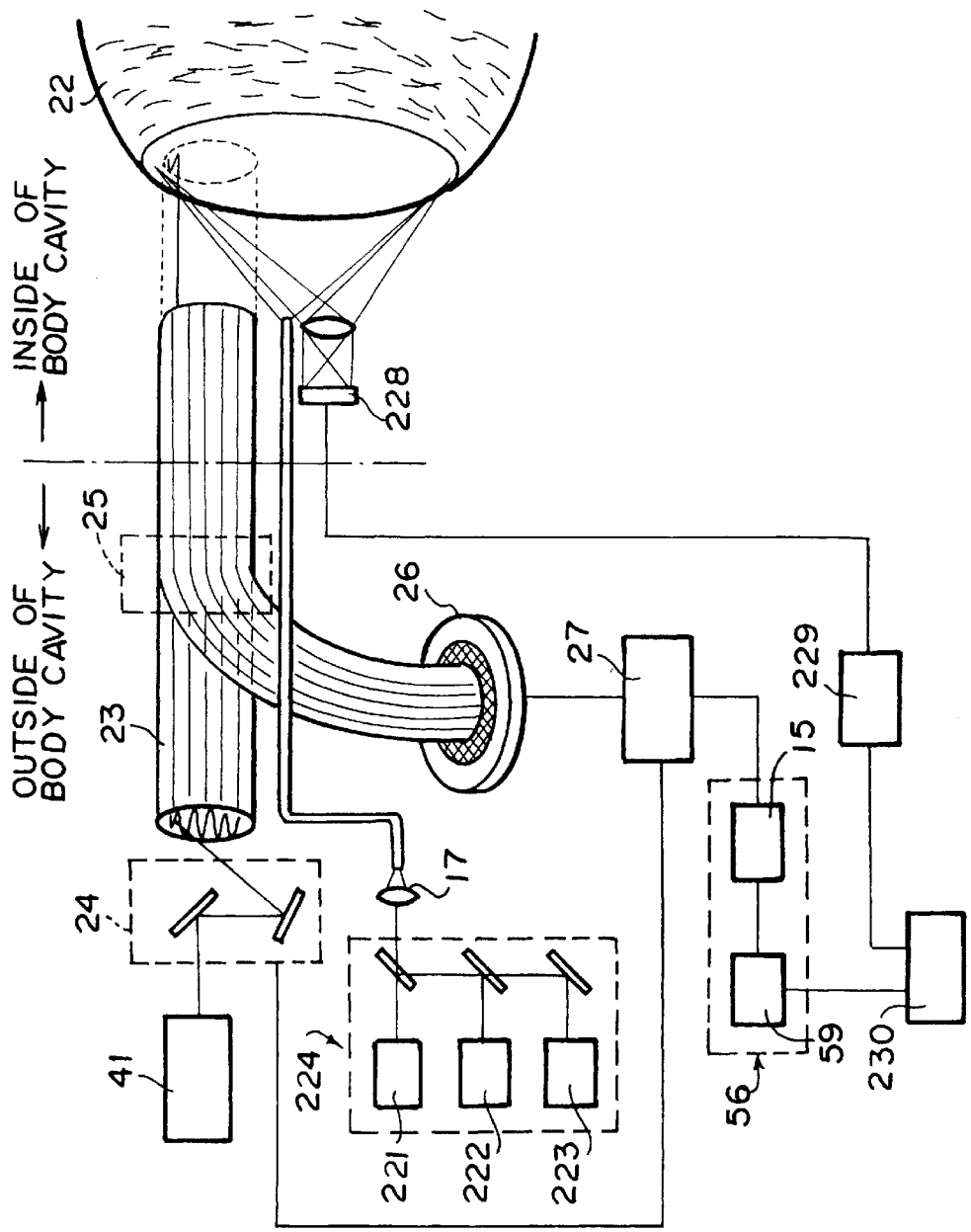
FIG. 14 is a block diagram showing a fourth embodiment of the image composing endoscope in accordance with the present invention.

FIG. 14 is a block diagram showing a fourth embodiment of the image composing endoscope in accordance with the present invention. In FIG. 14, similar elements are numbered with the same reference numerals with respect to FIG. 12. The structure of the fourth embodiment of the image composing endoscope in accordance with the present invention is identical with the structure of the second embodiment of FIG. 12, except that the laser beam source 41 capable of producing at least two laser beams having different frequencies such that the frequencies of the laser beams may be swept with the passage of time, is employed in lieu of the frequency-sweep single frequency laser beam source 1 employed in the embodiment of FIG. 12. Also, the calculation processing means 15 and the reconstruction means 59 are employed in lieu of the reconstruction means 53, which is employed in the embodiment of FIG. 12.

Specifically, the calculation processing means 15 calculates values concerning constituents and/or functions of a portion, which is located at a specific depth from the inner surface of the sample 22, from at least two discriminated difference-frequency beat signals, the intensities of which repeatedly become high and low at predetermined frequencies and which are obtained when at least two laser beams having different frequencies and having been produced by the frequency-sweep laser beam source 41 are respectively irradiated to the sample 22. The reconstruction means 59 generates a deep portion image signal, which represents constituents and/or functions of the portion located at the specific depth from the inner surface of the sample 22, from the calculated values.

The reconstruction means 59 and the calculation processing means 15 together constitute a reconstructing section 56.

How the fourth embodiment of the image composing endoscope in accordance with the present invention operates will be described hereinbelow.

The frequency-sweep laser beam source 41 produces a first laser beam, the frequency of which is swept in the triangular wave form as indicated by the solid line in FIG. 7. The first laser beam, which has been produced by the laser beam source 41 is sequentially guided by the scanning means 24 to the entry ends of a plurality of fiber bundles, which constitute the image fiber bundle 23.

Thereafter, the same operations as those in the second embodiment of the image composing endoscope shown in FIG. 12 are carried out, and a difference-frequency beat signal, the intensity of which repeatedly becomes high and low at a predetermined frequency, is discriminated by the time series frequency analyzing means 27 from the plurality of kinds of the difference-frequency beat signals.

Thereafter, the laser beam source 41 produces a second laser beam having a frequency band different from the frequency band of the first laser beam. The frequency of the second laser beam is swept in the frequency-sweep wave form as indicated by the broken line in FIG. 7. In the same manner as that described above, a difference-frequency beat signal is discriminated which corresponds to the same depth in the sample 22 as the aforesaid specific depth associated with the difference-frequency beat signal that was obtained by irradiating the first laser beam to the sample 22.

Thereafter, in the same manner as that in the embodiment of FIG. 13, the deep portion image signal representing the constituents and/or functions at the specific depth in the sample 22 is generated.

The surface image output system and the CRT display device 230 operate in the same manner as those in the embodiment of FIG. 13. In this manner, an image is composed from the surface image of the sample 22 and the deep portion image representing the constituents and/or functions at the specific depth in the sample 22. The composed image is displayed on the CRT display device 230.

What is claimed is:

1. A deep portion visualizing endoscope comprising:

i) flexible fiber bundle having an entry end, from which light is entered into the fiber bundle, and a radiating end, from which the light having been entered into the fiber bundle is radiated out and which is inserted into the region inside of a sample to be viewed, ii) a light source for producing the light, which is to be entered into the fiber bundle from the entry end, wherein said light source is a frequency-sweep laser beam source which produces a laser beam to be entered into the fiber bundle from the entry end, iii) an image signal forming means disposed at the radiating end of said fiber bundle for causing the laser beam, which has been irradiated to the region inside of the sample and which has then been reflected from reflection planes of the sample, and a second laser beam, which has been split from the laser beam by said image signal forming means before being reflected from the reflection planes of the sample and which has traveled by a predetermined optical path length, to interfere with each other, and for obtaining an image signal composed of a plurality of different difference-frequency beat signals such that the frequencies, at which the intensities of the difference-frequency beat signals repeatedly become high and low, vary in accordance with the difference between deaths of the reflection planes from the inner surface of the sample, and iv) an image reproducing means for discriminating a difference-frequency beat signal, the intensity of which repeatedly becomes high and low at a predetermined frequency, from the image signal, and reproducing an image of a reflection plane, which is located at a predetermined depth from the inner surface of the sample, from the discriminated difference-frequency beat signal, and further comprising:

an optical path splitting means for splitting the laser beam before being entered into the fiber bundle from the entry end into two laser beams having planes of polarization, which planes of polarization are approximately normal to each other, and a first wavefront matching means for matching the wave fronts of the two laser beams, which have been split by the optical path splitting means, with each other before the two split laser beams are entered into the fiber bundle from the entry end, a wavefront-matched laser beam being thereby obtained, wherein said image signal forming means comprises:

a second wavefront matching means for splitting the wavefront-matched laser beam, which has been radiated out of the radiating end of the fiber bundle, into two laser beams having planes of polarization, which planes of polarization are approximately normal to each other, such that one of the two split laser beams travels by the predetermined optical path length, and such that the other laser beam is irradiated to and reflected by the sample, the second wavefront matching means thereafter matching the wave front of the laser beam, which has traveled by the predetermined optical path length, with the wave front of the laser beam, which has been irradiated to and reflected by the sample, a polarization means for causing the components of the two laser beams subjected to the wavefront matching by the second wavefront matching means, which components have an identical direction of polarization, to interfere with each other, and a two-dimensional optical intensity detecting means for detecting a plurality of different difference-frequency beat signals obtained from the interference such that the frequencies, at which the intensities of the difference-frequency beat signals repeatedly become high and low, may vary, and wherein said image reproducing means comprises:

a frequency analyzing means for discriminating a difference-frequency beat signal, the intensity of which repeatedly becomes high and low at a predetermined frequency, from the plurality of different difference-frequency beat signals, a reconstruction means for reconstructing an image of a portion, which is located at specific depth from the inner surface of the sample, from the discriminated difference-frequency beat signal, the intensity of which repeatedly becomes high and low at the predetermined frequency, and an image output means, which outputs the image having been reconstructed by the reconstruction means.

2. A deep portion visualizing endoscope as defined in claim 1 wherein a rotation means is provided which rotates the second wavefront matching means, the polarization means, and the two-dimensional optical intensity detecting means together around an axis, which is approximately parallel to the optical path of the laser beam having been radiated out of the radiating end of the fiber bundle.

3. A function diagnosing endoscope comprising:

i) a flexible fiber bundle having an entry end, from which light is entered into the fiber bundle, and a radiating end, from which the light having been entered into the fiber bundle is radiated out and which is inserted into the region inside of a sample to be viewed, ii) a light source for producing the light, which is to be entered into the fiber bundle from the entry end, wherein the light source is a frequency-sweep laser beam source capable of producing at least two laser beams having different frequencies, which laser beams are to be sequentially entered into the fiber bundle from the entry end, the frequencies of the laser beams being swept with the passage of time, iii) an image signal forming means disposed at the radiating end of said bundle for causing a laser beam, which as been irradiated to the region inside of the sample and which has been reflected from reflection planes of the sample, and a second laser beam, which has been split from the laser beam by said image signal forming means before being reflected from the reflection planes of the sample and which has traveled by a predetermined optical path length, to interfere with each other, and thereby obtaining an image signal composed of a plurality of different difference-frequency beat signals such that the frequencies, at which the intensities of the difference-frequency beat signals repeatedly become high and low, vary in accordance with the difference between depths of the reflection planes from the inner surface of the sample, and iv) and image reproducing means for discriminating a difference-frequency beat signal, the intensity of which repeatedly becomes high and low at a predetermined frequency, from the image signal, and for calculating values concerning constituents and/or functions of a reflection plane, which is located at a predetermined depth from the inner surface of the sample, from at least two discriminated difference-frequency beat signals, the intensities of which repeatedly become high and low at predetermined frequencies and which are obtained when at least two laser beams having different frequencies are respectively irradiated to the sample, the image reproducing means thereafter reproducing an image, which represents constituents and/or functions of the sample, from the calculated values, and further comprising:

an optical path splitting means for splitting the laser beam before being entered into the fiber bundle from the entry end into two laser beams having planes of polarization, which planes of polarization are approximately normal to each other, and a first wavefront matching means for matching the wave fronts of the two laser beams, which have been split by the optical path splitting means, with each other before the two split laser beams are entered into the fiber bundle from the entry end, a wavefront-matched laser beam being thereby obtained, wherein said image signal forming means comprises:

a second wavefront matching means for splitting the wavefront-matched laser beam, which has been radiated out of the radiating end of the fiber bundle, into two laser beams having planes of polarization, which planes of polarization are approximately normal to each other, such that one of the two split laser beams may travel by the predetermined optical path length, and such that the other laser beam may be irradiated to and reflected by the sample, the second wavefront matching means thereafter matching the wave front of the laser beam, which has traveled by the predetermined optical path length, with the wave front of the laser beam, which has been irradiated to and reflected by the sample, a polarization means for causing the components of the two laser beams subjected to the wavefront matching by the second wavefront matching means, which components have an identical direction of polarization, to interfere with each other, and a two-dimensional optical intensity detecting means for detecting a plurality of different difference-frequency beat signals obtained from the interference such that the frequencies, at which the intensities of the difference-frequency beat signals repeatedly become high and low, may vary, and wherein said image reproducing means comprises:

a frequency analyzing means for discriminating a difference-frequency beat signal, the intensity of which repeatedly becomes high and low at a predetermined frequency, from the plurality of different difference-frequency beat signals, a reconstruction means for calculating values concerning constituents and/or functions of a portion, which is located at a specific depth from the inner surface of the sample, from at least two discriminated difference-frequency beat signals, the intensities of which repeatedly become high and low at predetermined frequencies and which are obtained when a least two laser beams having different frequencies are respectively irradiated to the sample, the reconstruction means thereafter reconstructing an image, which represents constituents and/or functions of the portion located at the specific depth from the inner surface of the sample, from the calculated values, and an image output means, which outputs the image having been reconstructed by the reconstruction means.

4. A function diagnosing endoscope as defined in claim 3 wherein a rotation means is provided which rotates the second wavefront matching means, the polarization means, and the two-dimensional optical intensity detecting means together around an axis, which is approximately parallel to the optical path of the laser beam having been radiated out of the radiating end of the fiber bundle.

* * * * *